(12) United States Patent
Yazdanpanah et al.

(10) Patent No.: US 10,858,333 B2
(45) Date of Patent: *Dec. 8, 2020

(54) SINGLE STEP LACTIDE PRODUCTION PROCESS WITH SEPARATE ENTRY FOR SOLVENT

(71) Applicant: Total Research & Technology Feluy, Seneffe (BE)

(72) Inventors: Mahdi Yazdanpanah, Le Havre (FR); Jamal Chaouki, Montréal (CA); Pieter Van Wouwe, Heverlee (BE); Bert Sels, Balen (BE)

(73) Assignee: TOTAL RESEARCH & TECHNOLOGY FELUY, Seneffe (BE)

( * ) Notice: Subject to any disclaimer, the term of this patent is extended or adjusted under 35 U.S.C. 154(b) by 0 days.

This patent is subject to a terminal disclaimer.

(21) Appl. No.: 16/309,964

(22) PCT Filed: Jun. 20, 2017

(86) PCT No.: PCT/EP2017/065000
§ 371 (c)(1),
(2) Date: Dec. 14, 2018

(87) PCT Pub. No.: WO2017/220519
PCT Pub. Date: Dec. 28, 2017

(65) Prior Publication Data
US 2019/0169156 A1 Jun. 6, 2019

(30) Foreign Application Priority Data
Jun. 20, 2016 (EP) .................................. 16175244

(51) Int. Cl.
*C07D 319/12* (2006.01)
*B01J 19/18* (2006.01)

(52) U.S. Cl.
CPC ........ *C07D 319/12* (2013.01); *B01J 19/1862* (2013.01); *B01J 2219/0004* (2013.01); *B01J 2219/00031* (2013.01)

(58) Field of Classification Search
CPC .................................................. C07D 319/12
See application file for complete search history.

(56) References Cited

U.S. PATENT DOCUMENTS

| 2013/0267716 A1 | 10/2013 | Hong et al. | |
| 2019/0169155 A1* | 6/2019 | Yazdanpanah | B01J 19/1862 |
| 2019/0330174 A1* | 10/2019 | Yazdanpanah | C07D 319/12 |

FOREIGN PATENT DOCUMENTS

| DE | 4407036 A1 | 9/1995 |
| WO | 9319058 A2 | 9/1993 |
| WO | 2014122294 A1 | 8/2014 |

OTHER PUBLICATIONS

Dusslier, M., et al. "Shape-selective zeolite catalysis for bioplastics production." Science. (Jul. 3, 2015), vol. 349, Issue 6243, pp. 78-80. (Year: 2015).*
International Search Report issued in PCT/EP2017/065000, dated Sep. 8, 2017, 4 pages.
Cichocki, et al., "Synthesis and Characterization of Boralites with MFI structure"; Zeolites 1990, 10, pp. 577-582.
Klinowski, "Recent Advances in Solid-State NMR of Zeolites" Ann. Rev. Mater. Sci. 1988, 18, pp. 189-218.
D. Trong On et al. "Titanium Boralites with MFI structure Characterized Using XRD, IR, UV-VIS Xanes and MAS-NMR Techniques" Studies in Surface Science and Catalysis 1995, 97, 535-541.
D. Trong On et al. Titanium Boralites with MFI structure Characterized Using XRD, Xanes, IR, and UV-Visible Techniques: Effect of Hydrogen Peroxide on the Preparation; Journal of Catalysis, Nov. 1995, vol. 157, Issue 1, pp. 235-243.
Groen et al., "Pore size determination in modified micro- and mesoporous materials. Pitfalls and limitations in gas adsorption data analysis", Microporous and Mesoporous Materials 2003, 60, pp. 1-17.
Storck et al., "Characterization of micro- and mesoporous solids by physisorption methods and pore-size analysis"; Applied Catalysis A: General 1998, 174, pp. 137-146.
Rouquerol et al. (Rouquerol F, Rouquerol J and Sing K, Adsorption by powders and porous solids: principles, methodology and applications, Academic Press, London, 1999).
Remy et al., "Dealuminated H-Y Zeolites: Relation between Physicochemical Properties and Catalytic Activity in Heptane and Decane Isomerization", J. Phys. Chem. 1996, 100, pp. 12440-12447.
Handbook of Heterogeneous Catalysis, second edition, edited by G. Ertl, H. Knözinger, F. Schüth and J. Weitkamp, Wiley 2008; pp. 1096-1122.

(Continued)

*Primary Examiner* — John S Kenyon
(74) *Attorney, Agent, or Firm* — Albert Shung

(57) ABSTRACT

The present invention relates to a process for synthesizing lactide, comprising the steps of:
  adding thermal energy to at least one solvent;
  providing one or more components to at least one reactor, the one or more components comprising lactic acid and the at least one solvent;
  converting at least part of the lactic acid into lactide and water; and
  recovering at least part of the lactide;
wherein the step of adding thermal energy to the at least one solvent is performed prior to the step of adding the at least one solvent to the at least one reactor;
wherein the at least one solvent is provided in the at least one reactor independently from the lactic acid by a separate entry into the at least one reactor; and,
wherein the step of converting at least part of the lactic acid into lactide and water is performed in one step.

13 Claims, 9 Drawing Sheets

(56) References Cited

OTHER PUBLICATIONS

G. Engelhardt and D. Michel, "High-Resolution Solid-State NMR of Silicates and Zeolites"; John Wiley & Sons, Chichester 1987.
Verified synthesis of zeolitic materials, 2nd Edition, H. Robson; Elsevier; 2001.
J. Weitkamp, "Zeolites and catalysis"; Solid State Ionics 2000, 131, pp. 175-188.
C Baerlocher, LB McCusker, DH Olson, "Atlas of Zeolite Framework Types" 6th ed. Elsevier, Amsterdam, 2007.

* cited by examiner

SINGLE STEP LACTIDE PRODUCTION PROCESS WITH SEPARATE ENTRY FOR SOLVENT

CROSS-REFERENCE TO RELATED APPLICATIONS

This application claims the benefit of PCT/EP2017/065000 filed Jun. 20, 2017, which claims priority from EP 16175244.9 filed Jun. 20, 2016, which are incorporated herein by reference in their entireties for all purposes.

TECHNICAL FIELD

The present invention relates to an industrial process for the single step preparation of lactide from lactic acid.

BACKGROUND

Polylactic acid (PLA), a renewable resource mainly obtained from corn starch and sugar cane, is one of the most important bio-based and biodegradable plastics, and may replace petroleum based plastics in a range of applications. For the production of PLA, lactic acid (LA) is typically first converted into lactide (LD), its cyclic dimer. Subsequently, this lactide is converted via ring opening polymerization into PLA. However, the most costly step is the conversion of lactic acid into lactide.

Currently, industrial lactide synthesis occurs mainly through a two-step process. A first step in the two-step process is the synthesis of a low quality lactic acid polymer. A second step is the conversion of this polymer into lactide via depolymerization, i.e. backbiting. This two-step process is typically energy consuming, selectivity is low, and significant amounts of meso-lactide, an undesired lactide, are generated. Alternatively, lactide may be synthesized in a gas-phase process over packed solid catalyst beds. Though cheaper than the two-step process, this industrial process has limited yield and/or limited volumetric productivity.

SUMMARY OF THE INVENTION

In view of the above, there is a need in the art to provide an alternative industrial process for the preparation of lactide from lactic acid. There is a need in the art to provide an industrial process for the preparation of lactide from lactic acid that is cheaper. There is a need in the art to provide an industrial process that is optimized in energy consumption and respects heat integration. There is a need in the art to provide an industrial process for the preparation of lactide from lactic acid that consumes less energy.

There is a need in the art to provide an industrial process for the preparation of lactide from lactic acid that is flexible. There is a need in the art to provide an industrial process for the preparation of lactide from lactic acid that is more selective. There is a need in the art to provide an industrial process for the preparation of lactide from lactic acid that has high yield. There is a need in the art to provide an industrial process for the preparation of lactide from lactic acid that has high volumetric productivity.

There is also a need in the art to provide a single step industrial process for the preparation of lactide from lactic acid that is flexible or independent with regards to the composition of the feed. There is also a need in the art to provide a single step industrial process for the preparation of lactide from lactic acid that is flexible that requires fewer heaters. There is also a need in the art to provide a single step industrial process for the preparation of lactide from lactic acid that has a simpler reactor design. There is also a need in the art to provide a single step industrial process for the preparation of lactide from lactic acid that has a simpler reactor design. There is also a need in the art to provide a single step industrial process for the preparation of lactide from lactic acid that has a smaller slurry pump.

There is also a need in the art to provide a single step industrial process for the preparation of lactide from lactic acid that has an improved product yield. There is also a need in the art to provide a single step industrial process for the preparation of lactide from lactic acid that has improved overall conversion.

There is also a need in the art to provide a single step industrial process for the preparation of lactide from lactic acid that has independent control of reactor settings. There is also a need in the art to provide a single step industrial process for the preparation of lactide from lactic acid that can still operate, with catalyst or without catalyst, in case of a technical malfunction. There is also a need in the art to provide a single step industrial process for the preparation of lactide from lactic acid that minimizes solvent. There is also a need in the art to provide a single step industrial process for the preparation of lactide from lactic acid that improves residence time.

There is also a need in the art to provide a single step industrial process for the preparation of lactide from lactic acid that is flexible or independent with regards to the composition of the feed. There is also a need in the art to provide a single step industrial process for the preparation of lactide from lactic acid that makes use of residual oligomers. There is also a need in the art to provide a single step industrial process for the preparation of lactide from lactic acid that is flexible or independent with regards to the concentration of oligomers in the feed. There is also a need in the art to provide a single step industrial process for the preparation of lactide from lactic acid that controls the water quantity that enters the reactor(s). There is also a need in the art to provide a single step industrial process for the preparation of lactide from lactic acid that controls the water quantity that enters the reactor(s). There is also a need in the art to provide a single step industrial process for the preparation of lactide from lactic acid that is flexible or independent with regards to the concentration of water in the feed. There is also a need in the art to provide a single step industrial process for the preparation of lactide from lactic acid that is flexible or independent with regards to the concentration of lactic acid in the feed. There is also a need in the art to provide a single step industrial process for the preparation of lactide from lactic acid that avoids or limits difficult and/or costly separation steps, for example for separating a catalyst from the lactic acid, for example by costly techniques such as filtration and/or centrifugation.

There is also a need in the art to provide a single step industrial process for the preparation of lactide from lactic acid that is energy efficient. There is also a need in the art to provide a single step industrial process for the preparation of lactide from lactic acid that avoids or limits the addition of water from an external source. There is also a need in the art to provide a single step industrial process for the preparation of lactide from lactic acid that avoids or limits the addition of catalyst from an external source.

There is also a need in the art to provide a single step industrial process for the preparation of lactide from lactic acid that reduces the cost of a separate catalyst regeneration step. There is also a need in the art to provide a single step industrial process for the preparation of lactide from lactic acid that can be operational both with and without catalyst, at little additional effort or cost.

There is also a need in the art to provide a single step industrial process for the preparation of lactide from lactic acid that is energy efficient. There is also a need in the art to provide a single step industrial process for the preparation of lactide from lactic acid wherein the energy input is minimal. There is also a need in the art to provide a single step industrial process for the preparation of lactide from lactic acid wherein the energy loss is minimal.

There is also a need in the art to provide a single step industrial process for the preparation of lactide from lactic acid with fewer steps for separating water. There is also a need in the art to provide a single step industrial process for the preparation of lactide from lactic acid wherein the separation of water is simpler and/or cheaper. There is also a need in the art to provide a single step industrial process for the preparation of lactide from lactic acid wherein the separation of water requires no or less additional heating. There is also a need in the art to provide a single step industrial process for the preparation of lactide from lactic acid with no or less degradation of the lactide. There is also a need in the art to provide a single step industrial process for the preparation of lactide from lactic acid with no or less degradation of the solvent. There is also a need in the art to provide a single step industrial process for the preparation of lactide from lactic acid wherein the separation of water is compatible with the catalyst used. The invention overcomes one or more of the above-mentioned needs. Preferred embodiments of the invention overcome one or more of the above-mentioned needs.

In general, the invention provides a process for synthesizing lactide, comprising the steps of: providing one or more components to at least one reactor, the one or more components comprising lactic acid; converting at least part of the lactic acid into lactide and water, preferably in one step; and recovering at least part of the lactide.

According to a first aspect, the invention provides a process for synthesizing lactide, preferably an industrial process for synthesizing lactide, comprising the steps of: adding thermal energy to at least one solvent; providing one or more components to at least one reactor, the one or more components comprising lactic acid and the at least one solvent; converting at least part of the lactic acid into lactide and water, preferably in one step; and recovering at least part of the lactide; wherein the step of adding thermal energy to the at least one solvent is performed prior to the step of adding the at least one solvent to the at least one reactor; and wherein the at least one solvent is provided in the at least one reactor independently from the lactic acid by a separate entry into the at least one reactor.

According to a second aspect, the invention provides a process for synthesizing lactide, preferably an industrial process for synthesizing lactide, comprising the steps of: providing one or more components to at least one reactor, the one or more components comprising lactic acid; converting at least part of the lactic acid into lactide and water and into lactic acid oligomers, preferably in one step; recovering at least part of the lactide; recovering at least part of the water and at least part of the lactic acid oligomers; adding a feed, optionally comprising lactic acid oligomers, and optionally comprising water, to the recovered water and the recovered lactic acid oligomers, and mixing the feed with the recovered water and the recovered lactic acid oligomers to form a mixture; converting at least part of the lactic acid oligomers in the mixture into lactic acid and into lactic acid dimer, preferably in one step; and removing at least part of the water from the mixture; whereby at least part of the remainder of the mixture is provided as one of the one or more components that are provided to the at least one reactor.

According to a third aspect, the invention provides a process for synthesizing lactide, preferably an industrial process for synthesizing lactide, comprising the steps of: adding thermal energy to at least one of one or more components; providing the one or more components to at least one reactor, the one or more components comprising lactic acid; converting at least part of the lactic acid into lactide and water, preferably in one step; recovering at least part of the lactide; recovering at least part of the thermal energy; and adding the recovered thermal energy to at least one of the one or more components.

According to a fourth aspect, the invention provides a process for synthesizing lactide, preferably an industrial process for synthesizing lactide, comprising the steps of: providing one or more components to at least one reactor, the one or more components comprising lactic acid; converting at least part of the lactic acid into lactide and water, preferably in one step; recovering at least part of the lactide; and recovering at least part of the water; wherein the step of recovering at least part of the water comprises a decantation step, preferably with the proviso that the step of recovering at least part of the water does not comprise an azeotropic distillation step.

BRIEF DESCRIPTION OF THE DRAWINGS

Following reference numbers are adhered to in FIG. 1: Original feed (100); Pumps (101,102,103,104), for example vacuum pump (104); Lactic acid, LA (110); Lactic acid dimer, L2A (120); Lactic acid oligomers, L3A, L4A, LxA (130); Water (140); Solvent (150); Catalyst system (160); Lactide (200); Lactide filter (210); Valve for lactide purification (215); Lactide purifier (220); Refrigeration cycle for lactide crystallization (300); First crystallization reactor (301); Second crystallization reactor (302); Compressor (310); Heat exchangers for refrigeration cycle (311, 312); Valve for refrigeration cycle (315); High quality water (400); Water separation between reactors (410); Decantation step (420); Water separation membrane (430); Steam generator (500); Optional heat exchanger for steam/feed (510); Heated steam for feed (511); Cooled steam from feed (512); Heat exchanger for steam/solvent (520); Heated steam for solvent (521); Cooled steam from solvent (522); First heat recovery step (610); Cold stream and hot stream sides of heat exchanger for first heat recovery step (611, 612); Second heat recovery step (620); Cold stream and hot stream sides of heat exchanger for second heat recovery step (621, 622); Third heat recovery step (630); Heat exchanger for third heat recovery step (632); First reactor (710); Second reactor (720); Optional recycling reactor or optional regeneration reactor (730)

DETAILED DESCRIPTION OF THE INVENTION

Figure 1A:
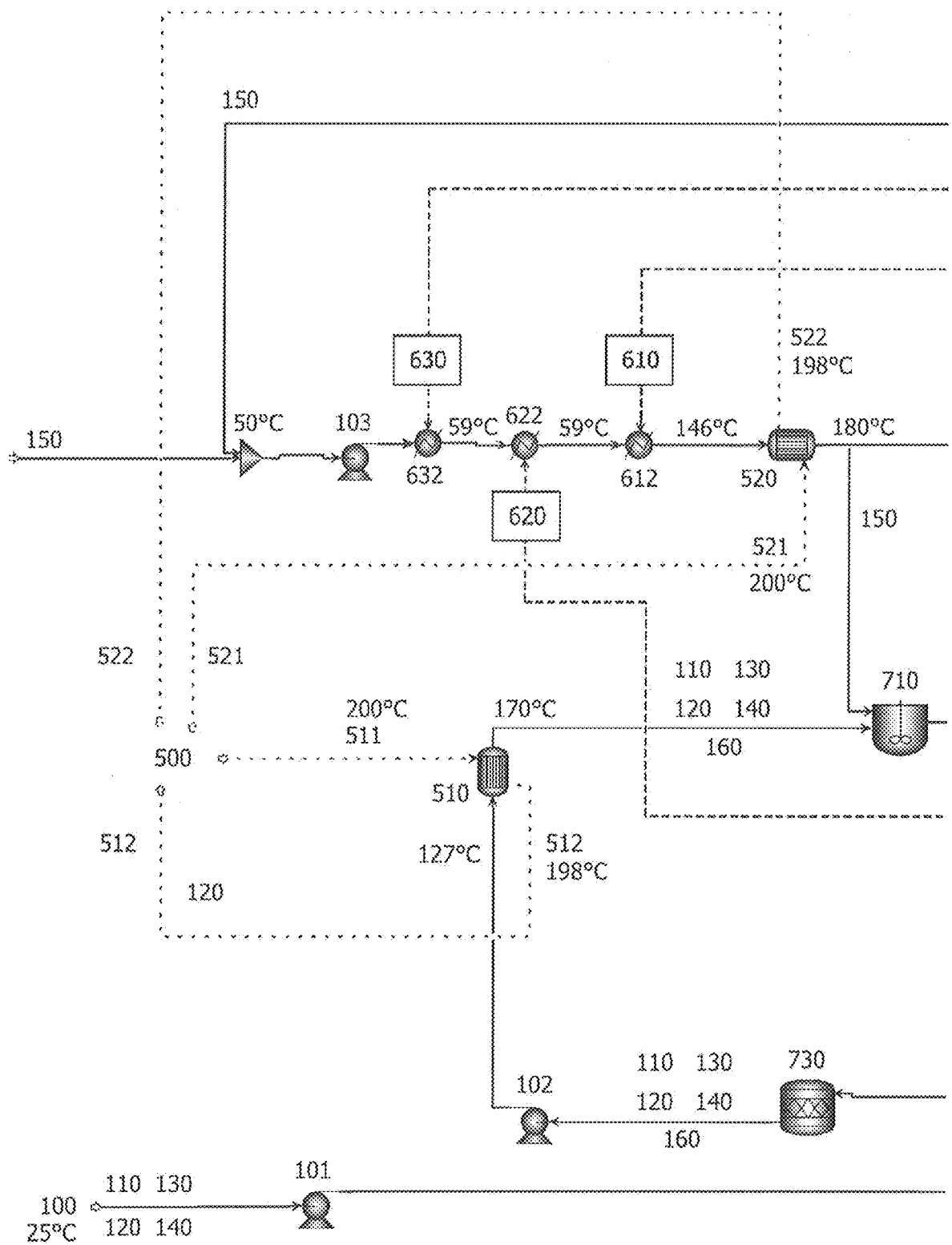
FIG. 1, composed of FIG. 1A, FIG. 1B, FIG. 1C, and FIG. 1D, represents flow diagram of a process, combining several preferred embodiments of the present invention.
Figure 1B:
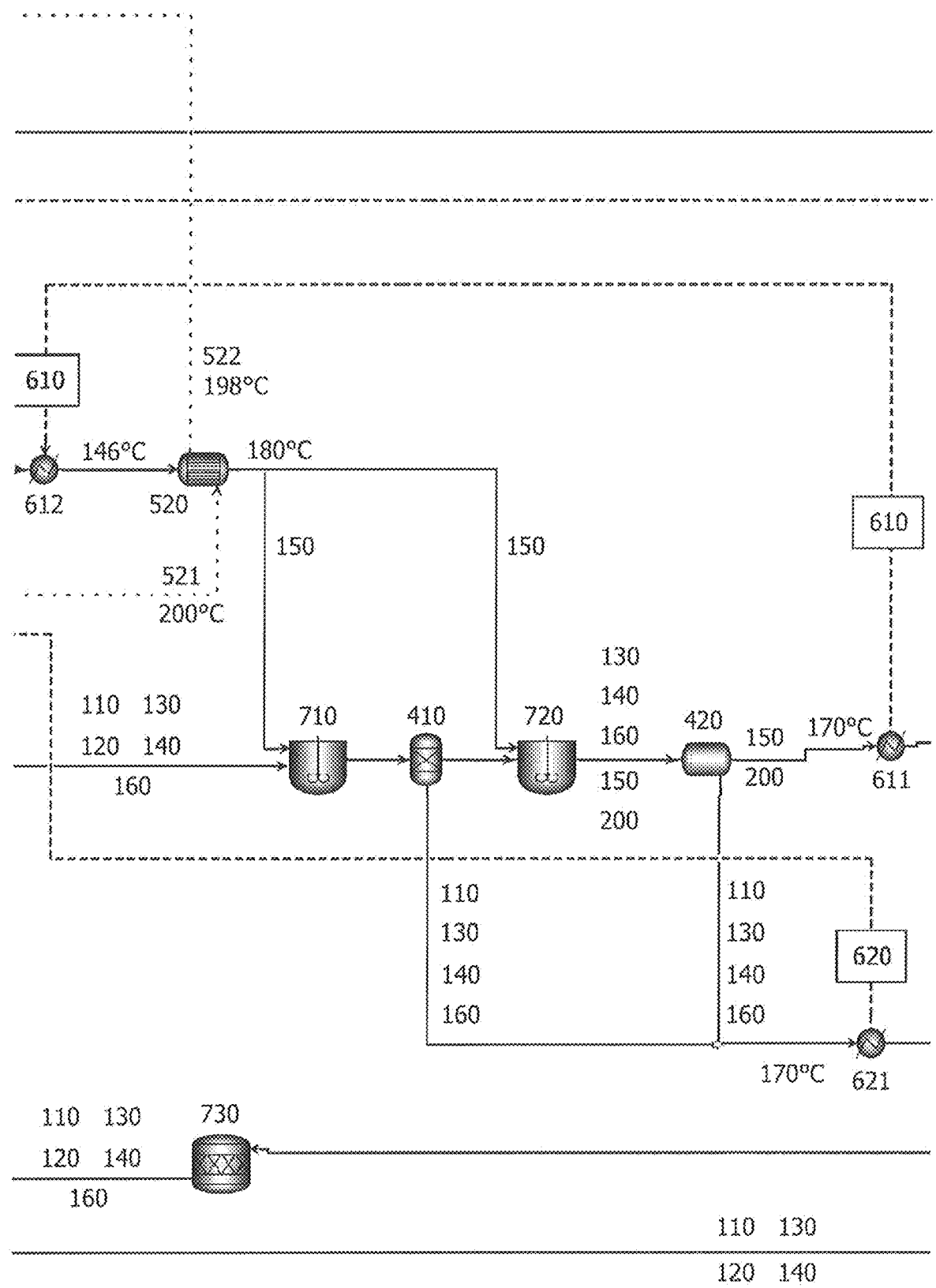
Figure 1C:
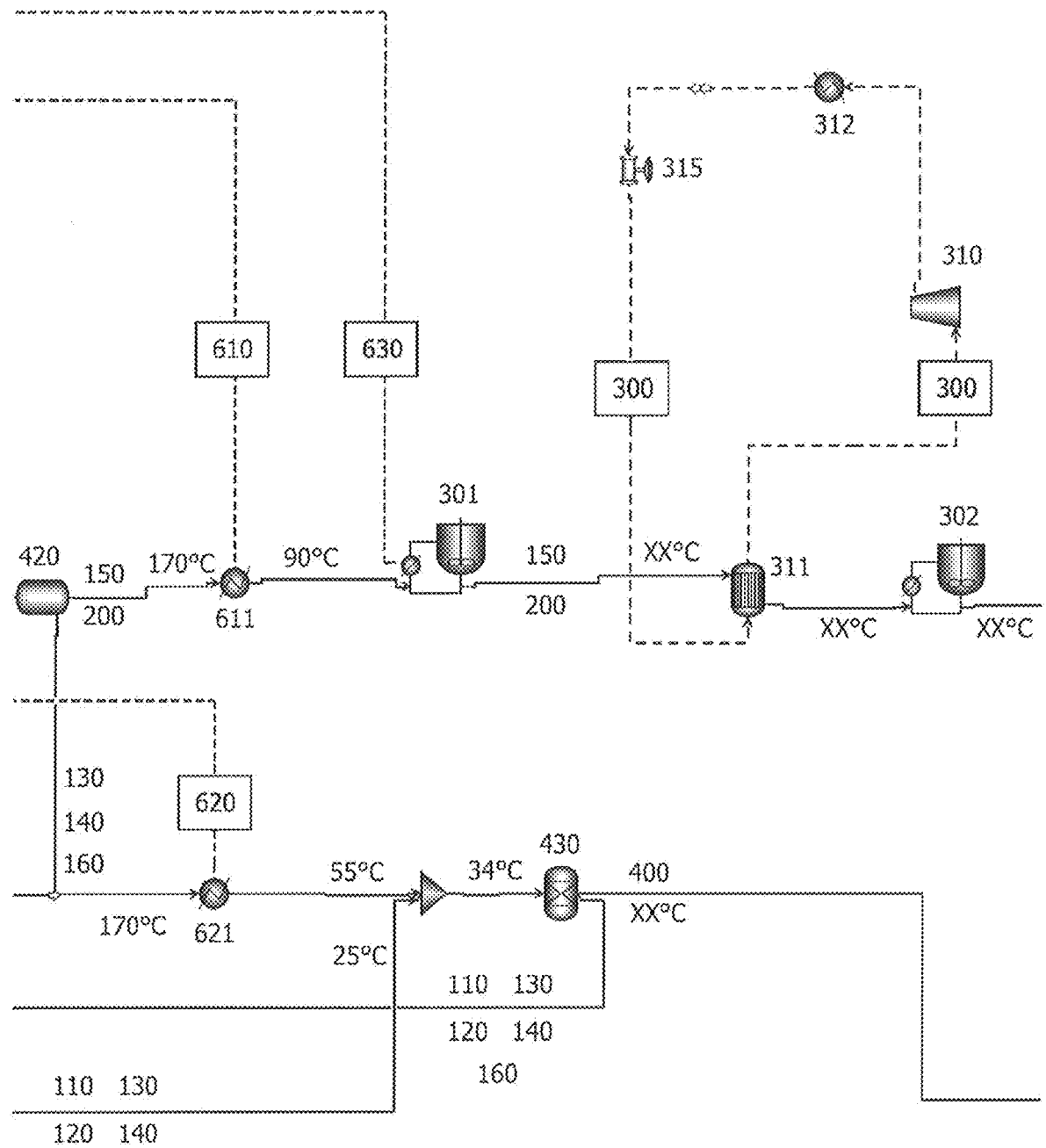
Figure 1D:
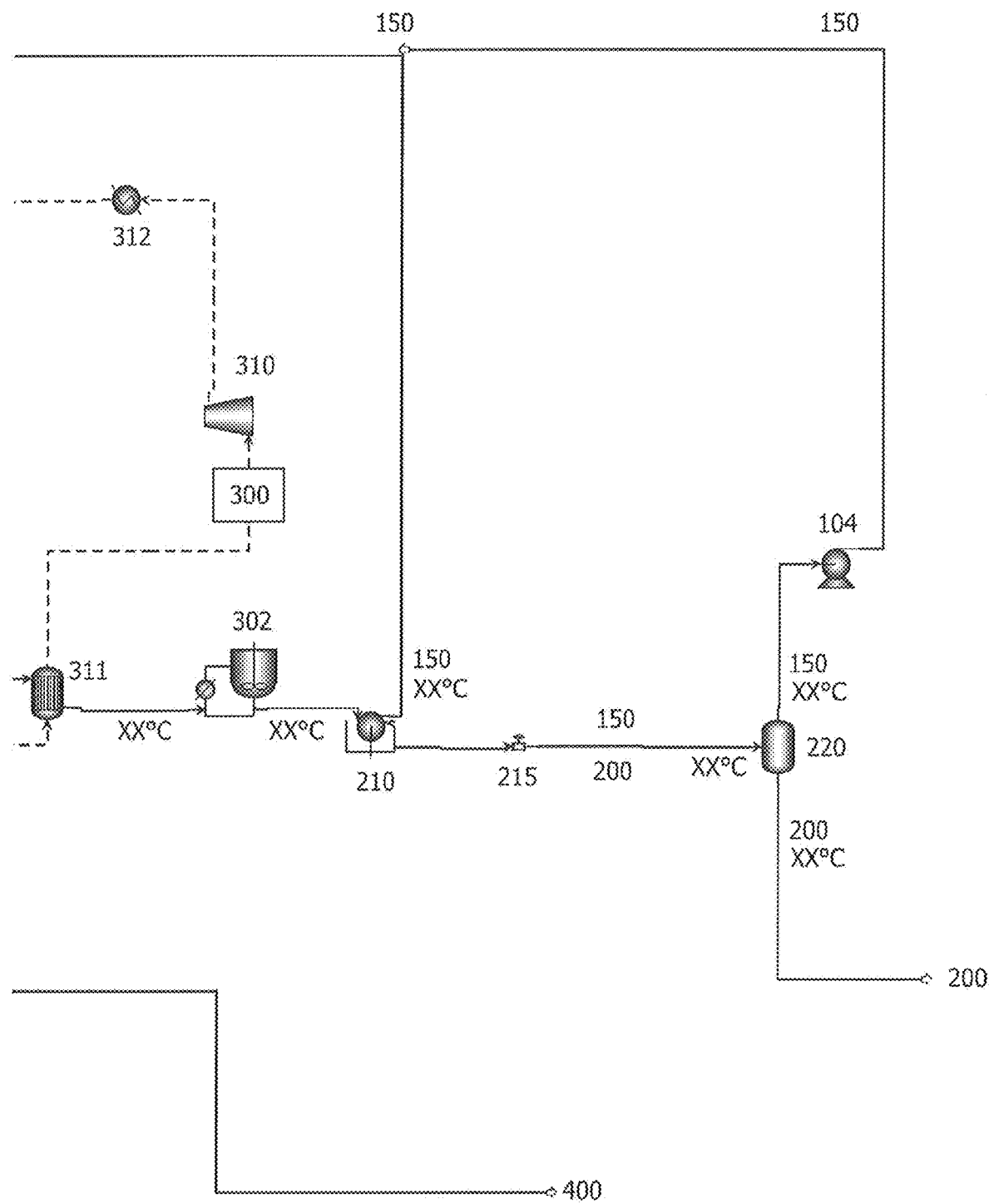

Before the present processes according to the present invention are described, it is to be understood that this invention is not limited to particular processes described, since such processes may, of course, vary. It is also to be understood that the terminology used herein is not intended to be limiting, since the scope of the present invention will be limited only by the appended claims.

When describing the invention, the terms used are to be construed in accordance with the following definitions, unless the context dictates otherwise.

As used herein, the singular forms "a", "an", and "the" include both singular and plural referents unless the context clearly dictates otherwise. By way of example, "a resin" means one resin or more than one resin. Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination. The terms "comprising", "comprises" and "comprised of" as used herein are synonymous with "including", "includes" or "containing", "contains", and are inclusive or open-ended and do not exclude additional, non-recited members, elements or method steps. It will be appreciated that the terms "comprising", "comprises" and "comprised of" as used herein comprise the terms "consisting of", "consists" and "consists of". The recitation of numerical ranges by endpoints includes all integer numbers and, where appropriate, fractions subsumed within that range (e.g. 1 to 5 can include 1, 2, 3, 4 when referring to, for example, a number of elements, and can also include 1.5, 2, 2.75 and 3.80, when referring to, for example, measurements). The recitation of end points also includes the end point values themselves (e.g. from 1.0 to 5.0 includes both 1.0 and 5.0). Any numerical range recited herein is intended to include all sub-ranges subsumed therein.

All references cited in the present specification are hereby incorporated by reference in their entirety. In particular, the teachings of all references herein specifically referred to are incorporated by reference.

Preferred statements (features) and embodiments of the processes and uses of this invention are set herein below. Each statements and embodiments of the invention so defined may be combined with any other statement and/or embodiments unless clearly indicated to the contrary. In particular, any feature indicated as being preferred or advantageous may be combined with any other feature or features or statements indicated as being preferred or advantageous. Hereto, the present invention is in particular captured by any one or any combination of one or more of the below numbered aspects and embodiments 1 to 139, with any other statement and/or embodiments.

1. Process for synthesizing lactide, preferably an industrial process for synthesizing lactide, comprising the steps of: providing one or more components to at least one reactor, the one or more components comprising lactic acid; converting at least part of the lactic acid into lactide and water, preferably in one step; and recovering at least part of the lactide.

2. Process for synthesizing lactide, preferably an industrial process for synthesizing lactide, comprising the steps of: adding thermal energy to at least one solvent; providing one or more components to at least one reactor, the one or more components comprising lactic acid and the at least one solvent; converting at least part of the lactic acid into lactide and water, preferably in one step; and recovering at least part of the lactide; wherein the step of adding thermal energy to the at least one solvent is performed prior to the step of adding the at least one solvent to the at least one reactor; and wherein the at least one solvent is provided in the at least one reactor independently from the lactic acid by a separate entry into the at least one reactor; preferably wherein the step of converting at least part of the lactic acid into lactide and water is performed in one step.

3. Process for synthesizing lactide, preferably an industrial process for synthesizing lactide, comprising the steps of: providing one or more components to at least one reactor, the one or more components comprising lactic acid; converting at least part of the lactic acid into lactide and water and into lactic acid oligomers, preferably in one step; recovering at least part of the lactide; recovering at least part of the water and at least part of the lactic acid oligomers; adding a feed, optionally comprising lactic acid oligomers, and optionally comprising water, to the recovered water and the recovered lactic acid oligomers, and mixing the feed with the recovered water and the recovered lactic acid oligomers to form a mixture; converting at least part of the lactic acid oligomers in the mixture into lactic acid and into lactic acid dimer, preferably in one step; and removing at least part of the water from the mixture; whereby at least part of the remainder of the mixture is provided as one of the one or more components that are provided to the at least one reactor; preferably wherein the step of converting at least part of the lactic acid into lactide and water is performed in one step.

4. Process for synthesizing lactide, preferably an industrial process for synthesizing lactide, comprising the steps of: adding thermal energy to at least one of one or more components; providing the one or more components to at least one reactor, the one or more components comprising lactic acid and preferably at least one solvent; converting at least part of the lactic acid into lactide and water, preferably in one step; recovering at least part of the lactide; preferably recovering at least part of the at least one solvent; recovering at least part of the thermal energy, preferably wherein at least part of the recovered thermal energy is recovered from the recovered solvent; and adding the recovered thermal energy to at least one of the one or more components, preferably in the first and/or second listed step.

5. Process for synthesizing lactide, preferably an industrial process for synthesizing lactide, comprising the steps of: providing one or more components to at least one reactor, the one or more components comprising lactic acid and preferably a solvent; converting at least part of the lactic acid into lactide and water, preferably in one step; recovering at least part of the lactide; and recovering at least part of the water; preferably wherein the step of converting at least part of the lactic acid into lactide and water is performed in one step; and wherein the step of recovering at least part of the water comprises a decantation step, preferably with the proviso that the step of recovering at least part of the water does not comprise an azeotropic distillation step.

6. Process for synthesizing lactide, preferably an industrial process for synthesizing lactide, comprising the steps of: providing one or more components to at least one reactor, the one or more components comprising lactic acid and at least one solvent; converting at least part of the lactic acid into lactide and water, preferably in one step; and recovering at least part of the lactide; wherein the at least one solvent is provided in the at least one reactor independently from the lactic acid by a separate entry into the at least one reactor.

7. Process for synthesizing lactide, preferably an industrial process for synthesizing lactide, comprising the steps of: adding thermal energy to at least one solvent; providing one or more components to at least one reactor, the one or more components comprising lactic acid and the at least one solvent; converting at least part of the lactic acid into lactide and water, preferably in one step; and recovering at least part of the lactide; wherein the step of adding thermal energy to the at least one solvent is performed prior to the step of adding the at least one solvent to the at least one reactor.

8. Process for synthesizing lactide, preferably an industrial process for synthesizing lactide, comprising the steps of: providing one or more components to at least two reactors, preferably to at least two reactors connected in series, the one or more components comprising lactic acid; converting at least part of the lactic acid into lactide and water, preferably in one step; and recovering at least part of the lactide.

9. Process for synthesizing lactide, preferably an industrial process for synthesizing lactide, comprising the steps of: providing one or more components to at least two reactors, preferably to at least two reactors connected in series, the one or more components comprising lactic acid and at least one solvent; converting at least part of the lactic acid into lactide and water, preferably in one step; and recovering at least part of the lactide; wherein the at least one solvent is divided into at least two solvent fractions, and wherein each solvent fraction is separately provided to each reactor of the at least two reactors.

10. Process for synthesizing lactide, preferably an industrial process for synthesizing lactide, comprising the steps of: providing one or more components to at least one reactor, the one or more components comprising lactic acid and at least one catalyst system; converting at least part of the lactic acid into lactide and water, preferably in one step; recovering at least part of the lactide; recovering at least part of the at least part of the water, optionally wherein the recovered water comprises at least part of at least one catalyst system; recovering at least part of the at least one catalyst system, optionally wherein the recovered catalyst system is comprised in at least part of the water; and regenerating at least part of the recovered catalyst system; wherein the step of regenerating at least part of the recovered catalyst system is performed through hydrolysis by the recovered water.

11. Process for synthesizing lactide, preferably an industrial process for synthesizing lactide, comprising the steps of: providing one or more components to at least one reactor, the one or more components comprising lactic acid; converting at least part of the lactic acid into lactide and water, preferably in one step; and recovering at least part of the lactide; wherein the step of recovering at least part of the lactide comprises a first crystallization step and a second crystallization step.

12. Process for synthesizing lactide, preferably an industrial process for synthesizing lactide, comprising the steps of: providing one or more components to at least one reactor, the one or more components comprising lactic acid; converting at least part of the lactic acid into lactide and water, preferably in one step; recovering at least part of the lactide; and recovering at least part of the water; wherein the step of recovering at least part of the water comprises a decantation step preferably with the proviso that the step of recovering at least part of the water does not comprise an azeotropic distillation step.

13. Process for synthesizing lactide, preferably an industrial process for synthesizing lactide, comprising the steps of: providing one or more components to at least one reactor, the one or more components comprising lactic acid; converting at least part of the lactic acid into lactide and water, preferably in one step; recovering at least part of the lactide; and purifying the recovered lactide; preferably wherein the step of purifying the recovered lactide comprises a combination of vacuum and heating, and/or wherein the step of purifying the recovered lactide comprises a purifying crystallization step.

14. Process according any one of the preceding statements, wherein the step of converting at least part of the lactic acid into lactide and water is performed in one step.

15. Process according to any one of the preceding statements, wherein the one or more components comprise at least one solvent.

16. Process according to any one of the preceding statements, wherein the one or more components comprise at least one catalyst system.

17. Process according to any one of the preceding statements, comprising the step of: recovering at least part of the water, optionally wherein the recovered water comprises at least part of the at least one catalyst system.

18. Process according to any one of the preceding statements, comprising the step of: recovering at least part of the at least one catalyst system, optionally wherein the recovered catalyst system is comprised in at least part of the water.

19. Process according to any one of the preceding statements, comprising the step of: recovering at least part of the water and at least part of the at least one catalyst system, wherein the recovered water comprises at least part of the at least one catalyst system.

20. Process according to any one of the preceding statements, comprising the step of: recovering at least part of the at least one solvent.

21. Process according to any one of the preceding statements, comprising the step of: converting at least part of the lactic acid into lactide and water and into lactic acid oligomers, preferably in one step; and recovering at least part of the lactic acid oligomers.

22. Process according to any one of the preceding statements, comprising the step of: adding thermal energy to at least one of the one or more components.

23. Process according to any one of the preceding statements, wherein the step of adding thermal energy to at least one of the one or more components is performed prior to the step of adding the one or more components to the at least one reactor.

24. Process according to any one of the preceding statements, comprising the step of: recovering thermal energy from at least one of the one or more recovered components.

25. Process according to any one of the preceding statements, comprising the step of: providing the one or more components to at least two reactors, preferably to at least two reactors connected in series.

26. Process according to any one of the preceding statements, comprising the steps of: adding thermal energy to at least one solvent; providing one or more components to at least one reactor, the one or more components comprising lactic acid and the at least one solvent; converting at least part of the lactic acid into lactide and water, preferably in one step; and recovering at least part of the lactide; wherein the step of adding thermal energy to the at least one solvent is performed prior to the step of adding the at least one solvent to the at least one reactor; and wherein the at least one solvent is provided in the at least one reactor independently from the lactic acid by a separate entry into the at least one reactor.

27. Process according to any one of the preceding statements, comprising the steps of: providing one or more components to at least one reactor, the one or more components comprising lactic acid; converting at least part of the lactic acid into lactide and water and into lactic acid oligomers, preferably in one step; recovering at least part of the lactide; recovering at least part of the water and at least part of the lactic acid oligomers; adding a feed, optionally comprising lactic acid oligomers, and optionally comprising water, to the recovered water and the recovered lactic acid oligomers, and mixing the feed with the recovered water and the recovered lactic acid oligomers to form a mixture; converting at least part of the lactic acid oligomers in the mixture into lactic acid and into lactic acid dimer, preferably in one step; and removing at least part of the water from the mixture; whereby at least part of the remainder of the mixture is provided as one of the one or more components that are provided to the at least one reactor.

28. Process according to any one of the preceding statements, comprising the steps of: adding thermal energy to at least one of one or more components; providing the one or more components to at least one reactor, the one or more components comprising lactic acid; converting at least part of the lactic acid into lactide and water, preferably in one step; recovering at least part of the lactide; recovering at least part of the thermal energy; and adding the recovered thermal energy to at least one of the one or more components.

29. Process according to any one of the preceding statements, comprising the steps of: providing one or more components to at least one reactor, the one or more components comprising lactic acid; converting at least part of the lactic acid into lactide and water, preferably in one step; recovering at least part of the lactide; and recovering at least part of the water; wherein the step of recovering at least part of the water comprises a decantation step, preferably with the proviso that the step of recovering at least part of the water does not comprise an azeotropic distillation step.

30. Process according to any one of the preceding statements, comprising the steps of: providing one or more components to at least one reactor, the one or more components comprising lactic acid and at least one solvent; converting at least part of the lactic acid into lactide and water, preferably in one step; and recovering at least part of the lactide; wherein the at least one solvent is provided in the at least one reactor independently from the lactic acid by a separate entry into the at least one reactor.

31. Process according to any one of the preceding statements, comprising the steps of: adding thermal energy to at least one solvent; providing one or more components to at least one reactor, the one or more components comprising lactic acid and the at least one solvent; converting at least part of the lactic acid into lactide and water, preferably in one step; and recovering at least part of the lactide; wherein the step of adding thermal energy to the at least one solvent is performed prior to the step of adding the at least one solvent to the at least one reactor.

32. Process according to any one of the preceding statements, comprising the steps of: providing one or more components to at least two reactors, preferably to at least two reactors connected in series, the one or more components comprising lactic acid; converting at least part of the lactic acid into lactide and water, preferably in one step; and recovering at least part of the lactide.

33. Process according to any one of the preceding statements, comprising the steps of: providing one or more components to at least two reactors, preferably to at least two reactors connected in series, the one or more components comprising lactic acid and at least one solvent; converting at least part of the lactic acid into lactide and water, preferably in one step; and recovering at least part of the lactide; wherein the at least one solvent is divided into at least two solvent fractions, and wherein each solvent fraction is separately provided to each reactor of the at least two reactors.

34. Process according to any one of the preceding statements, comprising the steps of: providing one or more components to at least one reactor, the one or more components comprising lactic acid and at least one catalyst system; converting at least part of the lactic acid into lactide and water, preferably in one step; recovering at least part of the lactide; recovering at least part of the at least part of the water, optionally wherein the recovered water comprises at least part of at least one catalyst system; recovering at least part of the at least one catalyst system, optionally wherein the recovered catalyst system is comprised in at least part of the water; and regenerating at least part of the recovered catalyst system; wherein the step of regenerating at least part of the recovered catalyst system is performed through hydrolysis by the recovered water.

35. Process according to any one of the preceding statements, comprising the steps of: providing one or more components to at least one reactor, the one or more components comprising lactic acid; converting at least part of the lactic acid into lactide and water, preferably in one step; and recovering at least part of the lactide; wherein the step of recovering at least part of the lactide comprises a first crystallization step and a second crystallization step.
36. Process according to any one of the preceding statements, comprising the steps of: providing one or more components to at least one reactor, the one or more components comprising lactic acid; converting at least part of the lactic acid into lactide and water, preferably in one step; recovering at least part of the lactide; and recovering at least part of the water; wherein the step of recovering at least part of the water comprises a decantation step with the proviso that the step of recovering at least part of the water does not comprise an azeotropic distillation step.
37. Process according to any one of the preceding statements, comprising the steps of: providing one or more components to at least one reactor, the one or more components comprising lactic acid; converting at least part of the lactic acid into lactide and water, preferably in one step; recovering at least part of the lactide; and purifying the recovered lactide; preferably wherein the step of purifying the recovered lactide comprises a combination of vacuum and heating, and/or wherein the step of purifying the recovered lactide comprises a purifying crystallization step.
38. Process according to any one of the preceding statements, wherein prior to the step of adding the at least one solvent to the at least one reactor, the solvent has a temperature of at least 140° C. and at most 300° C.; preferably of at least 150° C. and at most 250° C.; preferably of at least 160° C. and at most 220° C.
39. Process according to any one of the preceding statements, wherein prior to the step of adding the at least one solvent to the at least one reactor, the solvent has a temperature of at least 5° C. greater than the temperature of the lactic acid, preferably of at least 10° C. greater than the temperature of the lactic acid, preferably of at least 20° C. greater than the temperature of the lactic acid, preferably of at least 30° C. greater than the temperature of the lactic acid, preferably of at least 40° C. greater than the temperature of the lactic acid, preferably of at least 50° C. greater than the temperature of the lactic acid, preferably of at least 60° C. greater than the temperature of the lactic acid, preferably of at least 70° C. greater than the temperature of the lactic acid, preferably of at least 80° C. greater than the temperature of the lactic acid.
40. Process according to any one of the preceding statements, wherein prior to the step of adding the at least one solvent to the at least one reactor, the solvent has a temperature of at least 5° C. and at most 100° C. greater than the temperature of the lactic acid, preferably of at least 10° C. and at most 80° C. greater, and preferably of at least 15° C. and at most 50° C. greater.
41. Process according to any one of the preceding statements, wherein the one or more components are provided to at least two reactors, preferably to at least two reactors connected in series.
42. Process according to any one of the preceding statements, comprising the step of recovering at least part of the water, wherein the at least part of the water is recovered between the at least two reactors.
43. Process according to any one of the preceding statements, wherein at least 50% of the water is recovered between the at least two reactors, based on the total amount of water exiting the first reactor of the at least two reactors.
44. Process according to any one of the preceding statements, wherein the at least one solvent is divided into at least two solvent fractions, and wherein each solvent fraction is separately provided to each reactor of the at least two reactors.
45. Process according to any one of the preceding statements, wherein the at least two solvent fractions comprise a first solvent fraction and a second solvent fraction, and wherein at least part of the thermal energy is added to the first solvent fraction.
46. Process according to any one of the preceding statements, wherein the at least two solvent fractions comprise a first solvent fraction and a second solvent fraction, and wherein at least part of the thermal energy is added to the second solvent fraction.
47. Process according to any one of the preceding statements, comprising the steps of: providing a first solvent fraction comprising at least 50% and at most 100% of the at least one solvent, preferably at least 60% and at most 85% of the at least one solvent, to the first reactor of the at least two reactors; and providing a second solvent fraction comprising at least 0% and at most 50% of the at least one solvent, preferably at least 15% and at most 40% of the at least one solvent, to the second reactor of the at least two reactors; with % based on the total sum weight of the first solvent fraction and the second solvent fraction.
48. Process according to any one of the preceding statements, wherein the thermal energy added to the at least one solvent is at least partly recovered thermal energy, preferably wherein the partly recovered thermal energy was recovered from recovered solvent and/or recovered water.
49. Process according to any one of the preceding statements, wherein the one or more components provided to the at least one reactor comprises at least 1% by weight of lactic acid and at most 100% by weight of lactic acid, with % by weight based on the total weight of the one or more components, preferably at least 5% by weight and at most 95% by weight, preferably at least 15% by weight and at most 90% by weight.
50. Process according to any one of the preceding statements, wherein the step of converting at least part of the lactic acid oligomers in the mixture into lactic acid and into lactic acid dimer is performed through hydrolysis by the recovered water and/or through hydrolysis by water present in the feed.
51. Process according to any one of the preceding statements, wherein the one or more components comprise at least one catalyst system, and wherein the process comprises the steps of: providing at least one catalyst system to the at least one reactor; recovering at least part of the at least one catalyst system; and regenerating at least part of the recovered catalyst system.
52. Process according to any one of the preceding statements, wherein the step of regenerating at least part of the recovered catalyst system is performed through hydrolysis by the recovered water and/or through hydrolysis by water present in the feed.
53. Process according to any one of the preceding statements, wherein the at least one catalyst system is regenerated in-line with the at least one reactor.

54. Process according to any one of the preceding statements, wherein the at least one catalyst system comprises an acidic zeolite, preferably H-BEA.
55. Process according to any one of the preceding statements, wherein the step of removing at least part of the water from the mixture is performed with a membrane.
56. Process according to any one of the preceding statements, wherein the feed comprises lactic acid oligomers.
57. Process according to any one of the preceding statements, wherein the feed comprises at least 1% by weight lactic acid oligomers and at most 20% by weight lactic acid oligomers; preferably at least 5% by weight lactic acid oligomers and at most 15% by weight lactic acid oligomers; preferably about 10% by weight lactic acid oligomers; with % by weight compared to the total weight of lactic acid, lactic acid dimer, and lactic acid oligomers combined.
58. Process according to any one of the preceding statements, wherein the step of converting at least part of the lactic acid oligomers in the mixture into lactic acid and into lactic acid dimer, and optionally the step of regenerating at least part of the recovered catalyst system, is performed in one or more recycling pipes.
59. Process according to any one of the preceding statements, comprising the step of: recovering at least part of the water; wherein at least part of the recovered thermal energy is recovered from the recovered water.
60. Process according to any one of the preceding statements, wherein the one or more components comprise at least one solvent, comprising the step of: recovering at least part of the at least one solvent; wherein at least part of the recovered thermal energy is recovered from the recovered solvent.
61. Process according to any one of the preceding statements, wherein at least part of the recovered thermal energy is recovered from the recovered lactide.
62. Process to according to any one of the preceding statements, wherein the step of recovering at least part of the lactide comprises a first crystallization step and a second crystallization step.
63. Process according to any one of the preceding statements, wherein the first crystallization step and the second crystallization step are each independently cooled.
64. Process according to any one of the preceding statements, wherein the step of recovering at least part of the thermal energy is performed during the first crystallization step.
65. Process according to any one of the preceding statements, wherein the step of recovering at least part of the thermal energy is performed during the second crystallization step.
66. Process according to any one of the preceding statements, wherein at least part of the recovered thermal energy is added to the lactic acid.
67. Process according to any one of the preceding statements, wherein the one or more components comprise at least one solvent, and wherein at least part of the recovered thermal energy is added to the solvent.
68. Process according to any one of the preceding statements, wherein at least part of the recovered thermal energy is recovered from the recovered water, and wherein at least part of the recovered thermal energy is added to the lactic acid.
69. Process according to any one of the preceding statements, wherein at least part of the recovered thermal energy is recovered from the recovered water, and wherein at least part of the recovered thermal energy is added to the solvent.
70. Process according to any one of the preceding statements, wherein at least part of the recovered thermal energy is recovered from the recovered solvent, and wherein at least part of the recovered thermal energy is added to the lactic acid.
71. Process according to any one of the preceding statements, wherein at least part of the recovered thermal energy is recovered from the recovered solvent, and wherein at least part of the recovered thermal energy is added to the solvent.
72. Process according to any one of the preceding statements, wherein at least part of the recovered thermal energy is recovered from the recovered lactide, and wherein at least part of the recovered thermal energy is added to the lactic acid.
73. Process according to any one of the preceding statements, wherein at least part of the recovered thermal energy is recovered from the recovered lactide, and wherein at least part of the recovered thermal energy is added to the solvent.
74. Process according to any one of the preceding statements, wherein at least part of the recovered thermal energy is recovered from the recovered water, wherein at least part of the recovered thermal energy is recovered from the recovered solvent, wherein at least part of the recovered thermal energy is recovered from the recovered lactide, and wherein at least part of the recovered thermal energy is added to the solvent.
75. Process according to any one of the preceding statements, wherein the steps of:
    recovering at least part of the thermal energy, wherein at least part of the recovered thermal energy is recovered from the recovered solvent; and
    adding the recovered thermal energy to at least one of the one or more components;
    are performed with a heat exchanger.
76. Process according to any one of the preceding statements, with the proviso that the step of recovering at least part of the water does not comprise a liquid/liquid extraction step.
77. Process according to any one of the preceding statements, wherein the one or more components comprise at least one catalyst system and process comprises the step of: recovering at least part of the water, wherein the recovered water comprises at least part of at least one catalyst system.
78. Process according to any one of the preceding statements, wherein the at least one catalyst system comprises at least one acidic zeolite, preferably H-BEA.
79. Process according to any one of the preceding statements, comprising the step of: providing one or more components to at least two reactors, preferably to at least two reactors connected in series.
80. Process according to any one of the preceding statements, wherein the at least part of the water is recovered between the at least two reactors.
81. Process according to any one of the preceding statements, wherein the step of recovering at least part of the lactide is performed by crystallization, preferably wherein the step of recovering at least part of the lactide comprises a first crystallization step and a second crystallization step.

82. Process according to any one of the preceding statements, comprising the step of: purifying the recovered lactide.
83. Process according to any one of the preceding statements, wherein the step of purifying the recovered lactide comprises a combination of vacuum and heating.
84. Process according to any one of the preceding statements, wherein the step of purifying the recovered lactide is performed at a pressure of at most 200 mbar, preferably at most 100 mbar, for example of at least 20 mbar and at most 40 mbar, preferably of about 30 mbar.
85. Process according to any one of the preceding statements, wherein the step of purifying the recovered lactide is performed at a temperature of at most the melting point of lactide, preferably of at most 90° C., for example of at least 25° C. and at most 90° C.
86. Process according to any one of the preceding statements, wherein the step of purifying the recovered lactide comprises a purifying crystallization step.
87. Process according to any one of the preceding statements, wherein the one or more components comprise a solvent that is non-miscible with water, preferably wherein the solvent is isobutylbenzene or decane, preferably isobutylbenzene.
88. Process according to any one of the preceding statements, wherein the step of converting at least part of the lactic acid into lactide and water is performed in one step.
89. Process according to any one of the preceding statements, wherein the process is an industrial process for synthesizing lactide.
90. Process according to any one of the preceding statements, wherein the process is an industrial process for synthesizing lactide, and wherein the step of converting at least part of the lactic acid into lactide and water is performed in one step.
91. Process according to any one of the preceding statements, wherein the at least one reactor is a mixed reactor, preferably wherein the at least one reactor is mixed mechanically and/or with internal or external fluid flow.
92. Process according to any one of the preceding statements, wherein the at least two reactors are mixed reactors, preferably wherein the at least two reactors are mixed mechanically and/or with internal or external fluid flow.
93. Process according to any one of the preceding statements, wherein the step of adding thermal energy to at least one of the one or more components is performed after the step of adding the at least one of the one or more components to the at least one reactor, for example by an internal exchanger or a jacketed wall.
94. Process according to any one of the preceding statements, wherein the step of adding thermal energy to at least one of the one or more components is performed after the step of adding the at least one of the one or more components to the at least two reactors, for example by an internal exchanger or a jacketed wall.
95. Process according to any one of the preceding statements, wherein the step of recovering thermal energy is performed after the last reactor of the at least one reactor or after the last reactor of the at least two reactors.
96. Process according to any one of the preceding statements, wherein the step of recovering thermal energy is performed between reactors of the at least one reactor or after the last reactor of the at least two reactors.
97. Process according to any one of the preceding statements, wherein the step of recovering thermal energy is performed with a heat exchanger.
98. Process according to any one of the preceding statements, wherein the lactic acid is converted into lactide in a single reactor.
99. Process according to any one of the preceding statements, wherein the lactic acid is independently converted into lactide in each reactor of the at least two reactors.
100. Process according to any one of the preceding statements, comprising the step of recovering the at least one solvent, preferably comprising the step of recycling the at least one solvent.
101. Process according to any one of the preceding statements, wherein the at least one solvent is a $C_5$-$C_{24}$ alkane.
102. Process according to any one of the preceding statements, wherein the at least one solvent is decane.
103. Process according to any one of the preceding statements, wherein the at least one solvent is an aromatic solvent, preferably benzene, preferably substituted with one or more $C_1$-$C_4$ linear or branched alkyl groups.
104. Process according to any one of the preceding statements, wherein the at least one solvent is cumene, o-xylene, isobutylbenzene, p-xylene, or toluene, preferably wherein the at least one solvent is cumene, o-xylene, or isobutylbenzene, preferably wherein the at least one solvent is isobutylbenzene.
105. Process according to any one of the preceding statements, wherein the at least one catalyst system is dispersed in the at least one reactor in form of a slurry.
106. Process according to any one of the preceding statements, comprising the step of recovering the at least one catalyst system, preferably recycling the at least one catalyst system.
107. Process according to any one of the preceding statements, wherein the at least one catalyst system is regenerated by the solvent.
108. Process according to any one of the preceding statements, wherein the at least one catalyst system is regenerated through calcination.
109. Process according to any one of the preceding statements, performed in the absence of any catalyst system.
110. Process according to any one of the preceding statements, wherein the process is sometimes performed in the presence of at least one catalyst system and sometimes performed in the absence of any catalyst system.
111. Process according to any one of the preceding statements, wherein the at least one catalyst system comprises at least one acidic zeolite.
112. Process according to any one of the preceding statements, wherein the at least one catalyst system comprises at least one acidic zeolite comprising: two or three interconnected and non-parallel channel systems, wherein at least one of said channel systems comprises 10- or more-membered ring channels; and a framework $Si/X_2$ ratio of at least 24 as measured by NMR; or three interconnected and non-parallel channel systems, wherein at least two of said channel systems comprise 10- or more-membered ring channels; and a framework $Si/X_2$ ratio of at least 6 as measured by NMR; wherein each X is Al or B.
113. Process according to any one of the preceding statements, wherein at least one of the interconnected and non-parallel channel systems comprises 12- or more membered ring channels.
114. Process according to any one of the preceding statements, wherein the acidic zeolite has a Brønsted acid density between 0.05 and 6.5 mmol/g dry weight.
115. Process according to any one of the preceding statements, wherein X is Al.

116. Process according to any one of the preceding statements, wherein the acidic zeolite comprises at least three interconnecting and non-parallel channel systems.
117. Process according to any one of the preceding statements, wherein the acidic zeolite comprises a topology selected from the group comprising BEA, MFI, FAU, MEL, FER, and MWW, preferably BEA.
118. Process according to any one of the preceding statements, wherein the at least one catalyst system comprises an acidic zeolite, preferably wherein the at least one catalyst system comprises an H-BEA zeolite.
119. Process according to any one of the preceding statements, comprising the step of recovering at least part of the water, optionally wherein the water comprises at least part of the at least one catalyst system.
120. Process according to any one of the preceding statements, wherein the step of recovering at least part of the water comprises a distillation step.
121. Process according to any one of the preceding statements, wherein the step of recovering at least part of the water comprises a filtration step, preferably membrane filtration, for example through reverse osmosis.
122. Process according to any one of the preceding statements, wherein the step of recovering thermal energy is performed after the step of recovering at least part of the water.
123. Process according to any one of the preceding statements, wherein the lactic acid is obtained by bacterial fermentation of glucose or sucrose.
124. Process according to any one of the preceding statements, wherein the lactic acid is obtained by chemocatalytic transformation of trioses, hexoses, cellulose, or glycerol.
125. Process according to any one of the preceding statements, wherein the lactic acid comprises L-lactic acid.
126. Process according to any one of the preceding statements, wherein the lactic acid comprises D-lactic acid.
127. Process according to any one of the preceding statements, wherein the one or more components provided to the at least one reactor comprises at least 3% by weight of water and at most 95% by weight of water, with % by weight based on the total weight of the one or more components, preferably at least 5% by weight and at most 50% by weight, with % by weight based on the total weight of the one or more components provided to the at least one reactor, preferably at least 10% by weight and at most 30% by weight, with % by weight based on the total weight of the one or more components provided to the at least one reactor.
128. Process according to any one of the preceding statements, wherein the one or more components provided to the at least one reactor comprises at least 90% by weight of solvent, with % by weight based on the total weight of the one or more components, preferably at least 95% by weight, preferably at least 99.5% by weight.
129. Process according to any one of the preceding statements, wherein the mass flow rate of total quantity of solvent provided to all reactors is at least 4 times to at most 30 times the mass of lactic acid provided to all reactors, preferably at least 6 times to at most 25 times, preferably at least 9 to at most 20 times.
130. Process according to any one of the preceding statements, wherein the one or more components provided to the at least one reactor comprises at least 1% by weight of catalyst system and at most 25% by weight of catalyst system, with % by weight based on the total weight of the one or more components, preferably at least 3% by weight and at most 10% by weight, with % by weight based on the total weight of the one or more components provided to the at least one reactor.
131. In some embodiments, the one or more components provided to the at least one reactor comprises at most 1.00% by weight of organic acids other than lactic acid, preferably at most 0.10% by weight, preferably at most 0.01% by weight, with % by weight based on the total weight of the one or more components provided to the at least one reactor.
132. Process according to any one of the preceding statements, wherein the step of recovering at least part of the thermal energy is performed prior to the step of purifying the recovered lactide.
133. Process according to any one of the preceding statements, wherein the step of recovering at least part of the thermal energy is performed prior to the purifying crystallization step.
134. Process according to any one of the preceding statements, wherein the step of recovering at least part of the thermal energy is performed during the step of purifying the recovered lactide.
135. Process according to any one of the preceding statements, wherein the step of recovering at least part of the thermal energy is performed during the purifying crystallization step.
136. Process according to any one of the preceding statements, wherein the step of purifying the recovered lactide comprises a solvent-solvent extraction step.
137. Process according to any one of the preceding statements, wherein the step of purifying the recovered lactide comprises a filtration step, preferably through a membrane.
138. Process according to any one of the preceding statements, having a lactide yield of at least 60%, preferably at least 65%, preferably at least 70%, preferably at least 75%, preferably at least 80%, preferably at least 85%.
139. Process according to any one of the preceding statements, further comprising the step of: converting at least part of the recovered lactide into polylactic acid.

In what follows, the invention will be discussed in more detail. Explicitly exemplified and/or preferred embodiments of one aspect discussed below, should also be considered as explicitly exemplified and/or preferred embodiments for the other aspects discussed below.

The present invention relates to a process for synthesizing lactide, preferably an industrial process for synthesizing lactide. The process comprises the steps of: providing one or more components to at least one reactor, the one or more components comprising lactic acid; converting at least part of the lactic acid into lactide and water, preferably in one step; and recovering at least part of the lactide. Preferably, the step of converting at least part of the lactic acid into lactide and water is performed in one step.

In some embodiments, the one or more components comprise at least one solvent. In some embodiments, the one or more components comprise at least one catalyst system. In some embodiments, the one or more components comprise at least one solvent and at least one catalyst system.

In some embodiments, the process comprises the step of: recovering at least part of the water, optionally wherein the recovered water comprises at least part of the at least one catalyst system. In some embodiments, the process comprises the step of: recovering at least part of the at least one catalyst system, optionally wherein the recovered catalyst system is comprised in at least part of the water. In some embodiments, the process comprises the step of: recovering at least part of the water and at least part of the at least one catalyst system, wherein the recovered water comprises at least part of the at least one catalyst system.

In some embodiments, the process comprises the step of: recovering at least part of the at least one solvent.

In some embodiments, the process comprises the steps of: converting at least part of the lactic acid into lactide and water and into lactic acid oligomers, preferably in one step; and recovering at least part of the lactic acid oligomers.

In some embodiments, the process comprises the step of: adding thermal energy to at least one of the one or more components. In some embodiments, the step of adding thermal energy to at least one of the one or more components is performed prior to the step of adding the one or more components to the at least one reactor. In some embodiments, the process comprises the step of: recovering thermal energy from at least one of the one or more recovered components.

In some embodiments, the process comprises the step of: providing the one or more components to at least two reactors, preferably to at least two reactors connected in series.

In some particularly preferred embodiments, the invention provides a process for synthesizing lactide, comprising the steps of: adding thermal energy to at least one solvent; providing one or more components to at least one reactor, the one or more components comprising lactic acid and the at least one solvent; converting at least part of the lactic acid into lactide and water, preferably in one step; and recovering at least part of the lactide. The step of adding thermal energy to the at least one solvent is performed prior to the step of adding the at least one solvent to the at least one reactor.

Such a process has the advantage that heat is added to the solvent, which solvent is then used to (partially) heat the reactor(s). The amount of solvent and the temperature of the solvent can be modified to suit the lactic acid feed. This provides a more flexible process. Such a process also has the advantage that the reactor(s) requires less, or even no, heating elements. This allows for a cheaper and simpler reactor design. In addition, the heat exchanger on the feed and catalyst line can be removed and add all of the required thermal energy to the solvent flow. This reduces process CAPEX and improves the reliability regarding the fact that feed stream contains solid catalyst and it is better to reduce the unit operations on this line.

Another advantage is that such a process is more productive compared to a process that requires heat elements in the reactor, for example heat exchanger tubes. The process that occurs in a reactor without heating elements allows a better mixing because there are less or no obstacles in the reactor. Obstacles in the reactor, such as heating elements, disturb the movement of fluid or slurry in the reactor, creating zones in the reactor where the fluid is stationary or where the fluid is moving more slowly than normally in the reactor. In these zones, reagents may not be fed fast enough into the zone, reaction product is being built up in said zone, solid catalyst—if present—precipitates, and/or heat is not transferred in the same way as in other places in the reactor. All these events have an effect on the kinetics and the thermodynamics of the reaction, resulting in negative effects on the yield and the productivity of the reaction.

When using heating elements, the temperature in the direct zone around the heating element is often higher than the temperature in the rest of the reactor, and often higher than the optimal temperature for the reaction to occur. In this hot zone, side reactions can occur. An elevated temperature also promotes the formation of lactic acid oligomers, which lowers the overall yield of the lactide formation reaction.

Especially combined with the mixing deficiencies as described before, the heating elements can cause zones where the heat is not transferred properly, resulting in significant amounts of lactic acid oligomers.

Yet another advantage of such a process is that mixing requires less energy, because the preheated solvent causes a convective flow in the reactor.

Another advantage is noticeable when solids are present in the reaction mixture, for example an optional catalyst on a solid support. Said solids will collide with objects, such as heating elements, in the reactor.

These collisions will erode the objects in the reactor, shortening their lifespan. When the solids are catalyst particles, these particles will also undergo damage from the collision with the objects, reducing the lifespan of the catalyst. Avoiding the need for such objects in the reactor takes away these disadvantages and prolongs the lifespan of an optional catalyst. Furthermore, this may also prevent erosion of equipment that is placed in the reactor.

Use of two reactors in series may permit an increase of the overall process conversion, particularly in the case of adding an additional intermediate water separation step between the two reactors.

Separate entry of solvent and feed may permit to use the solvent flow for reactor heating and may avoid high heating of the feed. The heat exchanger on the feed entry may be totally eliminated. Instead, the solvent may be heated to higher temperatures to compensate this impact. This may reduce process CAPEX and may decrease process liability as less unit operations may be employed on the feed line which typically contains dispersed catalysts in slurry phase.

A solvent may be either injected only into the first reactor, or it may be divided into separate entries for each reactor. In this case, each reactor may be heated independently by adjusting the inlet flow rate of solvent in each reactor. This brings about the advantage of process flexibility in terms of temperature. In addition, the overall solvent volume in the first reactor may be less compared to the single entry case. Therefore, the available reactor volume for the feed may increase while the reactor volume is fixed. Therefore, the residence time of the reactants may increase and the overall conversion may be improved. Preferably, the solvent quantity remains above a minimum required solvent amount to dissolve all of the produced lactide.

In case of single entry for feed and solvent, a big slurry pump is typically used for whole fluids. By separating two fluids, a smaller slurry pump may be used for feed and catalyst inlet and another conventional pump may be used for the solvent inlet. In addition, regarding the fact that the feed line may have a lower pressure compared to the solvent line, less compression may be required for the solvent compared to the single pump condition. This results in OPEX saving.

The at least one solvent is provided in the at least one reactor independently from the lactic acid by a separate entry into the at least one reactor. Such a process also has the advantage that the heated solvent is independently added to the reactor(s) from the lactic acid feed. Such a process has the advantage that a smaller, slurry pump will be used, instead of a larger slurry pump. This allows for a cheaper, simpler and more reliable pump design.

In some preferred embodiments, prior to the step of adding the at least one solvent to the at least one reactor, the solvent has a temperature of at least 140° C. and at most 300° C.; preferably of at least 150° C. and at most 250° C.;

preferably of at least 160° C. and at most 210° C. The solvent may be used to heat up the reactor(s). The solvent may be used to heat up the other components provided to the reactor(s).

In some preferred embodiments, prior to the step of adding the at least one solvent to the at least one reactor, the solvent has a temperature of at least 5° C. greater than the temperature of the lactic acid, preferably of at least 10° C. greater than the temperature of the lactic acid, preferably of at least 20° C. greater than the temperature of the lactic acid, preferably of at least 30° C. greater than the temperature of the lactic acid, preferably of at least 40° C. greater than the temperature of the lactic acid, preferably of at least 50° C. greater than the temperature of the lactic acid, preferably of at least 60° C. greater than the temperature of the lactic acid, preferably of at least 70° C. greater than the temperature of the lactic acid, preferably of at least 80° C. greater than the temperature of the lactic acid. The solvent may be used to heat up the lactic acid.

In some preferred embodiments, prior to the step of adding the at least one solvent to the at least one reactor, the solvent has a temperature of at least 5° C. and at most 100° C. greater than the temperature of the lactic acid, preferably of at least 10° C. and at most 80° C. greater, and preferably of at least 15° C. and at most 50° C. greater.

In some preferred embodiments, the one or more components are provided to at least two reactors, preferably to at least two reactors connected in series. Such processes have the advantage that one of the reactors may be by-passed in case of a malfunction. Moreover, the overall reaction conversion increases thanks to use of reactors in series.

In some preferred embodiments, the process comprises the step of recovering at least part of the water, wherein the at least part of the water is recovered between the at least two reactors. Such processes permit water separation and increase the conversion in the second reactor. Such processes also reduce the risk of lactide hydrolysis into lactic acid. In some preferred embodiments, at least 50% of the water is recovered between the at least two reactors, based on the total amount of water exiting the first reactor of the at least two reactors, preferably by distillation, decantation, and/or filtration.

In some preferred embodiments, the at least one solvent is divided into at least two solvent fractions, wherein each solvent fraction is separately provided to each reactor of the at least two reactors. In some preferred embodiments, the at least two solvent fractions comprise a first solvent fraction and a second solvent fraction, wherein at least part of the thermal energy is added to the first solvent fraction. In some preferred embodiments, the at least two solvent fractions comprise a first solvent fraction and a second solvent fraction, wherein at least part of the thermal energy is added to the second solvent fraction. Such processes allow for a better control of the amount of solvent added to each reactor, and a better control of the amount of heat added to each solvent. This allows for an independent control of the reactor settings of each reactor. It also reduces the solvent content in the first reactor and hence increases the reactor volume available to the reactant. Therefore, the reactant residence time increases and consequently reaction conversion will improve.

Preferably, more solvent is added to the first reactor and less solvent is added to the second reactor. Such processes improve product yield and overall conversion. Such processes also improve the residence time of the components in the first reactor for identical reactor volume. Such processes also improve the overall conversion. In some preferred embodiments, the process comprises the steps of; providing a first solvent fraction comprising at least 50% and at most 100% of the at least one solvent, preferably at least 60% and at most 85% of the at least one solvent, to the first reactor of the at least two reactors; and providing a second solvent fraction comprising at least 0% and at most 50% of the at least one solvent, preferably at least 15% and at most 40% of the at least one solvent, to the second reactor of the at least two reactors; with % based on the total sum weight of the first solvent fraction and the second solvent fraction. Typically, the percentages add up to 100%. The amount of solvent added may depend on the solubility of lactide in the solvent. It is preferably at most 20 times the lactic acid content of feed, preferably at most 15 times, preferably at most 10 times, preferably at most 8 times, compared by weight.

In some preferred embodiments, the thermal energy added to the at least one solvent is at least partly recovered thermal energy, preferably wherein the partly recovered thermal energy was recovered from recovered solvent and/or recovered water. This allows for energetic optimization as also discussed elsewhere in the present description.

In some particularly preferred embodiments, the invention provides a process for synthesizing lactide comprising the steps of: providing one or more components to at least one reactor, the one or more components comprising lactic acid; converting at least part of the lactic acid into lactide and water and into lactic acid oligomers, preferably in one step; recovering at least part of the lactide; recovering at least part of the water and at least part of the lactic acid oligomers; adding a feed, optionally comprising lactic acid oligomers, and optionally comprising water, to the recovered water and the recovered lactic acid oligomers, and mixing the feed with the recovered water and the recovered lactic acid oligomers to form a mixture; converting at least part of the lactic acid oligomers in the mixture into lactic acid and into lactic acid dimer, preferably in one step; and removing at least part of the water from the mixture; whereby at least part of the remainder of the mixture is provided as one of the one or more components that are provided to the at least one reactor. Lactic acid dimer may also be known as L2A, lactyl lactate, or lactoyl lactate, shown in formula (I).

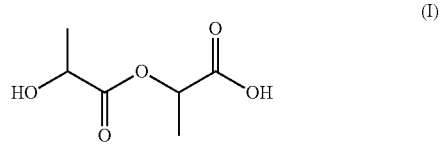

(I)

The process may add the water that is obtained after the reaction to the original lactic acid feed. Subsequently, a quantity of water is preferably removed, to provide a fixed amount of water in the feed that enters the reactor(s). Such a process has the advantage that the water content of the feed actually added to the reactor(s), is independent of the water content of the original feed, since the water quantity that enters reactor is separately controlled. Typically, the original feed will have a wide range of possible concentrations for lactic acid, which may range from 1% to 100% by weight of the total original feed, typically from 5% to 95%, typically from 15% to 90%. Such a process leads to an increased flexibility of the process, depending on the original feed, for identical or similar production capacity. Such a process also has the advantage that no distillation for the separation lactic acid, and an optional catalyst, from water is required. For example, separation by membrane may be sufficient. Such a process also has the advantage that the water is typically under pressure, and the separation is therefore efficient. In addition, water is hot in this case and this enhances the hydrolysis of the feed oligomers to lactic acid and lactic acid dimer to produce the reactants of Lactide production reaction. There is furthermore no need to add water from an external source. Furthermore, the high temperature of water is advantageous for catalyst regeneration with this water.

Mixing the feed with a water line after a decantation step, permits to increase the temperature of the feed and its water concentration to ease the hydrolysis of the oligomers. This ease in hydrolysis may avoid a separate cracking step for the oligomers to convert them into starting material. Hence a separation step may be avoided, no separate equipment may need to be foreseen for the cracking step, no reagents may need to be supplied to the separate cracking step, and/or no energy may need to be used for the separate cracking step, Mixing feed and the water containing line from a decantation step permits to recover the heat content of this stream by heating. Therefore, feed may be heated without use of an additional heat exchanger. In addition, the temperature of the flow into the water separation step may be reduced. This may results in easier water separation and less heat loss via separated water. The process allows using a single water separation step, and preferably one single water separator, to at least partially dewater the feed and to at least partially dewater the recovered water that comprises at least part of the lactic acid oligomers.

In some preferred embodiments, the one or more components provided to the at least one reactor comprises at least 1% by weight of lactic acid and at most 100% by weight of lactic acid, with % by weight based on the total weight of the one or more components, preferably at least 5% by weight and at most 95% by weight, preferably at least 15% by weight and at most 90% by weight. Because the quantity of water is controlled prior to entering the reactor (s), the quantity of lactic acid in the original feed may fluctuate.

In some preferred embodiments, the step of converting at least part of the lactic acid oligomers in the mixture into lactic acid and into lactic acid dimer is performed through hydrolysis by the recovered water and/or through hydrolysis by water present in the feed. During the reaction, oligomers be formed, herein referred to as L3A, L4A, etc. Such oligomers are typically not converted to lactide, in the presence of lactic acid. Such oligomers may also clog the pores of a zeolite catalyst. Using the water as a carrier solvent, accumulated oligomers could be removed. In addition, with the same water, they may be hydrolyzed back to lactic acid, herein referred to as LA, or to the dimer of lactic acid, herein referred to as L2A. By using such a regeneration strategy, all carbon coming from the reaction compounds can be reintroduced into the system, without any losses. The inventors have found that relatively short reaction times may be required to remove and convert all carbon originating from the feedstock: oligomers were typically removed after 15 min of extraction. This allows for efficient process, without the need of separating the oligomers and hydrolyzing the oligomers separately or forming lactide from the oligomers separately. The oligomers may be hydrolyzed back to LA and L2A on-the-fly.

In some preferred embodiments, the one or more components comprise at least one catalyst system, and wherein the process comprises the steps of: providing at least one catalyst system to the at least one reactor; recovering at least part of the at least one catalyst system; and regenerating at least part of the recovered catalyst system.

In some preferred embodiments, the step of regenerating at least part of the recovered catalyst system is performed through hydrolysis by the recovered water and/or through hydrolysis by water present in the feed. For example, when a zeolite catalyst is used, the zeolite may be regenerated by the water. The zeolite typically retrieves its initial activity after such processes. Such processes have the advantage that the water is typically hot (and possibly under pressure), and the reaction is therefore efficient. There is furthermore no need to add water from an external source.

In some preferred embodiments, the at least one catalyst system is regenerated in-line with the at least one reactor. This allows for efficient process, without the need of separating the catalyst and regenerating the catalyst separately. The catalyst may be regenerated on-the-fly. Such processes have the advantage that the catalyst cycle is closed. It is therefore possible to work without external catalyst source, or even without a catalyst. In some preferred embodiments, the at least one catalyst system comprises an acidic zeolite, preferably H-BEA. Acidic zeolites, and H-BEA in particular, are well-suited for regeneration through hydrolysis, particularly with the present water at elevated temperatures.

In some preferred embodiments, the step of removing at least part of the water from the mixture is performed with a membrane.

In some preferred embodiments, the feed comprises lactic acid oligomers (LxA, wherein x is equal to or greater than 3). Such processes have the advantage that the lactic acid oligomers in the feed are converted into lactic acid and lactic acid dimer by the water at elevated temperature, prior to being fed to the reactor. Furthermore, the zeolite catalyst may also catalyze the hydrolysis of oligomers in the zeolite itself, providing autocatalyzed regeneration. In some preferred embodiments, the feed comprises at most 50% by weight lactic acid oligomers; preferably most 15% by weight lactic acid oligomers; preferably about 10% by weight lactic acid oligomers; with % by weight compared to the total weight of lactic acid, lactic acid dimer, and lactic acid oligomers combined. Concentration of oligomers can rise up to 55% (including L2, L3, Lx . . . ) in case of a solution with initial 100% LA. The optimum case is where 30% is water, 60% LA, 9% L2A, and 1.0% LxA.

In some preferred embodiments, the step of converting at least part of the lactic acid oligomers in the mixture into lactic acid and into lactic acid dimer, and optionally the step of regenerating at least part of the recovered catalyst system, is performed in one or more recycling pipes. Such processes have the advantage that no separate regeneration reactor is required. Additional heating may be provided to the recycling pipes.

Mixing the feed with the water line after the decantation step permits to increase the temperature of the feed and its water concentration to ease the hydrolysis of the oligomers. Mixing feed and the water containing line from the decantation step permits to recover the heat content of this stream by heating.

Therefore, feed is heated without use of an additional heat exchanger. In addition, the temperature of the flow into the water separation step will be reduced. This may result in easier water separation and less heat loss via separated water.

In some particularly preferred embodiments, the invention provides a process for synthesizing lactide, comprising the steps of: adding thermal energy to at least one of one or more components; providing the one or more components to at least one reactor, the one or more components comprising lactic acid; converting at least part of the lactic acid into lactide and water, preferably in one step; recovering at least part of the lactide; recovering at least part of the thermal energy; and adding the recovered thermal energy to at least one of the one or more components. Such a process has the advantage that it is not too energy consuming.

The term "one step reaction" refers to a reaction wherein reagents are transformed in the desired reaction products by passing through one or more transition states, without the formation of intermediates that are be isolated and separated from the rest of the reaction mixture. Typically, a one step reaction is performed in one reactor with a single set of reaction conditions.

The term "two step reaction" refers to a reaction wherein reagents are transformed in the desired reaction products by passing through at least one first transition state to form an intermediate, followed by passing through at least one second transition state, before yielding the desired product. Different reaction conditions can be used to reach the at least first transition state than the reaction condition to reach the at least one second transition state. Said intermediate can be isolated and separated from the rest of the reaction mixture. Typically, a two step reaction is performed in two or more (sequential) reactors, each with an independent set of reaction conditions.

In some preferred embodiments, the process comprises the step of: recovering at least part of the water; wherein at least part of the recovered thermal energy is recovered from the recovered water.

In some preferred embodiments, the one or more components comprise at least one solvent, and the process comprises the step of: recovering at least part of the at least one solvent; wherein at least part of the recovered thermal energy is recovered from the recovered solvent.

Direct heat recovery from the solvent may be limited to a minimum temperature in range of 80° C. to 130° C. depending on the solvent nature and solubility of for example decane in the solvent. Cooling the solvent below this temperature limit may result in crystallization of the lactide inside the heat exchangers. Preferably, the heat from the crystallization step is recovered to heat the inlet fluids into the reactor. Crystallization may be carried out in more than one step to ease heat recovery.

The energy in the water containing line separated in the decantation step may be recovered to minimize the heat loss via the water outlet from the water separation unit. This energy may be recovered by heating the feed thanks to mixing the feed and the water containing line from decantation. This energy recovery may be done by use of a heat exchanger on this line as well. In this case CAPEX may increase as an additional heat exchanger is required.

In some preferred embodiments, at least part of the recovered thermal energy is recovered from the recovered lactide. In some preferred embodiments, the step of recovering at least part of the lactide comprises a first crystallization step and a second crystallization step. In some preferred embodiments, the first crystallization step and the second crystallization step are each independently cooled. In some preferred embodiments, the step of recovering at least part of the thermal energy is performed during the first crystallization step. In some preferred embodiments, the step of recovering at least part of the thermal energy is performed during the second crystallization step. Such processes have the advantage that the heat extraction necessary for crystallizing the lactide is used to heat up components that are provided to the reactor(s). In some preferred embodiments, at least part of the recovered thermal energy is added to the lactic acid. In some preferred embodiments, the one or more components comprise at least one solvent, and at least part of the recovered thermal energy is added to the solvent.

In some preferred embodiments, at least part of the recovered thermal energy is recovered from the recovered water, and at least part of the recovered thermal energy is added to the lactic acid. This is preferably performed by direct mixing of the feed and the separated water from decantation. Therefore no heat exchanger is required, which reduces CAPEX.

In some preferred embodiments, at least part of the recovered thermal energy is recovered from the recovered water, and at least part of the recovered thermal energy is added to the solvent. In some preferred embodiments, at least part of the recovered thermal energy is recovered from the recovered solvent, and at least part of the recovered thermal energy is added to the lactic acid. In some preferred embodiments, at least part of the recovered thermal energy is recovered from the recovered solvent, and at least part of the recovered thermal energy is added to the solvent. In some preferred embodiments, at least part of the recovered thermal energy is recovered from the recovered lactide, and at least part of the recovered thermal energy is added to the lactic acid. In some preferred embodiments, at least part of the recovered thermal energy is recovered from the recovered lactide, and at least part of the recovered thermal energy is added to the solvent.

In some preferred embodiments, at least part of the recovered thermal energy is recovered from the recovered water, at least part of the recovered thermal energy is recovered from the recovered solvent, at least part of the recovered thermal energy is recovered from the recovered lactide, and at least part of the recovered thermal energy is added to the solvent. Heat recovery to the solvent provides a heated solvent. Advantages of a heated solvent are described above.

Such processes, individually and/or combined, have the advantage that the individual processes are energetically optimized, and/or that the overall process is energetically optimized.

Preferably, at least 40% of the thermal energy is recovered from the flows leaving the reactor, preferably at least 50%, preferably at least 60%, preferably at least 70%. Heat exchangers may be used. The type of heat exchanger may differ, but is preferably selected from the group comprising tube and shell heat exchanger, plate heat exchanger, plate and shell heat exchanger, adiabatic wheel heat exchanger, plate fin heat exchanger, fluid heat exchangers, waste heat recovery units, dynamic scraped surface heat exchanger, phase-change heat exchangers, direct contact heat exchangers or microchannel heat exchangers; more preferably a counter current heat exchanger; most preferably a tube and shell counter current heat exchanger or a plate heat exchanger.

In some particularly preferred embodiments, the invention provides a process for synthesizing lactide, comprising the steps of: providing one or more components to at least one reactor, the one or more components comprising lactic acid; converting at least part of the lactic acid into lactide and water, preferably in one step; recovering at least part of the lactide; and recovering at least part of the water; wherein the step of recovering at least part of the water comprises a decantation step, with the proviso that the step of recovering at least part of the water does not comprise an azeotropic distillation step.

Such a process has the advantage that a multi-step recovery of water may not be required. Such a process has the advantage that no heating is needed. Such a process has the advantage that it does not degrade the lactide thermally. Such a process has the advantage that it does not degrade the solvent, which may be reused. Decantation of the separated catalyst in addition to the water separation may be performed thanks to the usually hydrophilic nature of catalyst. In addition catalyst regeneration may start in this section thanks to high temperature and the fact that the catalyst will be in a water phase.

Preferably, both water and catalyst are separated from the solvent stream. Integrated water and catalyst separation may reduce the energy consumption and process costs. Oligomers and unreached reactants may be separated from the solvent to a large extent by the water stream.

The contact between the water and separated catalyst inside the decanter permits to hydrolyze the oligomers inside the catalyst and to start catalyst regeneration inside a decanter. This is especially interesting regarding the high water temperature in this unit which enhances oligomer hydrolysis.

In some preferred embodiments, the one or more components comprise at least one catalyst system and process comprises the step of: recovering at least part of the water, wherein the recovered water comprises at least part of at least one catalyst system. In some preferred embodiments, the at least one catalyst system comprises at least one acidic zeolite, preferably H-BEA. Preferred zeolites are as described further below. The decantation step is particularly efficient with a hydrophilic catalyst such as a zeolite.

Figure 3A:
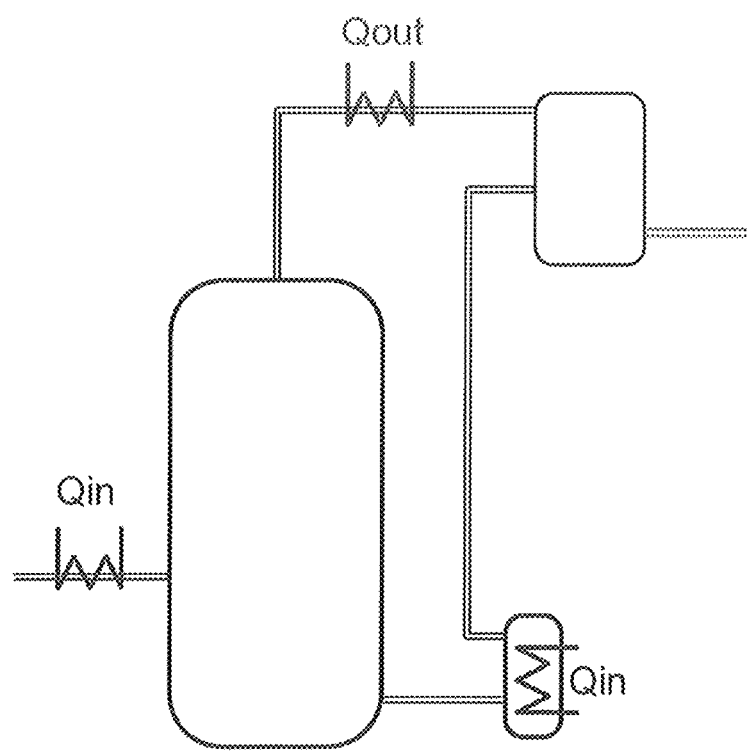
FIG. 3 composed of FIG. 3A, FIG. 3B, and FIG. 3C, illustrates possible reactor configurations to include in situ water separation and heat recovery.
FIG. 3B illustrates the use of two condensation steps: the first vessel operates at a temperature below the boiling point of the solvent (but higher than the boiling point of water) to recover mostly the solvent, while the second vessel operates at a temperature below the boiling point of water to recover water and remaining trace of solvent which is sent back into the reactor.
FIG. 3C illustrates an in situ separation of solvent, which is implanted inside the reactor by adding some distillation steps to separate solvent and return it back into the reactor.
Figure 3B:
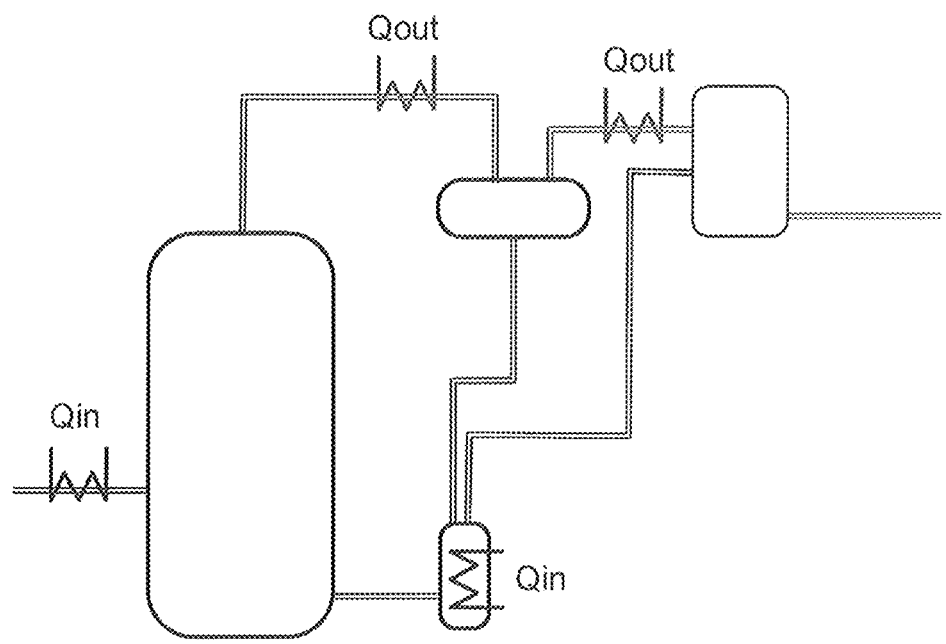
Figure 3C:
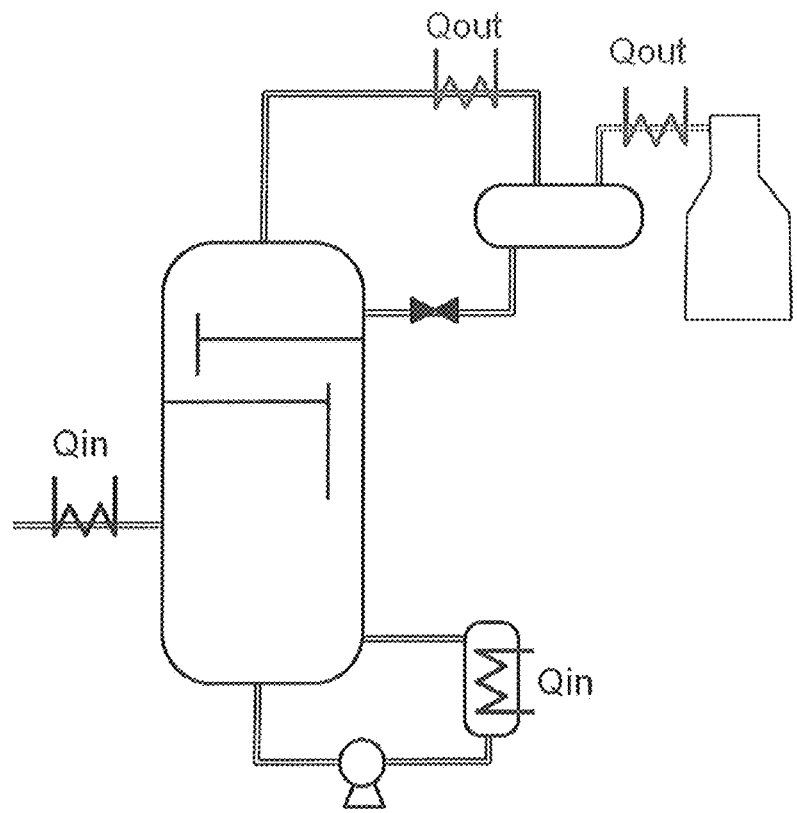

As an alternative to decantation, a distillation option may be provided directly into the reactor for in situ water separation. Various kinds of reactive distillation reactors may be used in this case. FIG. 3 shows some possible configurations. Depending on the nature of the solvent, other kind of designs may be used.

Some advanced distillation systems such as divided wall column may be used to produce a concentrated lactide outlet stream inside the reactor to ease the downstream separation steps. The energy consumption may be reduced by use of heat integration, to recover the evaporation energy which is inherent to the distillation.

In some preferred embodiments, the process comprises the step of: providing one or more components to at least two reactors, preferably to at least two reactors connected in series. In some preferred embodiments, the at least part of the water is recovered between the at least two reactors.

In some preferred embodiments, the step of recovering at least part of the lactide is performed by crystallization, preferably wherein the step of recovering at least part of the lactide comprises a first crystallization step and a second crystallization step. The second crystallizer may be cooled partially or completely with cold water depending on the availability of cooling water.

In some embodiments, the crystallizer design results in formation of solids in form of solid crystals with a specific adjustable particle size (the technology used for sugar grain production). This design may require a solid separation step, which could be filtration or centrifugal separation, among others. In some embodiments, the filtration technology will be relatively challenging regarding the fact that the separated particles may need to be continuously separated and recovered. This may be solved by an automated filtration system or centrifugal separation. Centrifugal separation has the advantage of operating in continuous mode. The difficulty would be agglomeration of LD particles and formation of a cohesive cake.

This can be resolved by controlling the outlet pressure and temperature of the centrifugation unit to fluidize the separated solid LD on the walls of the unit.

In some preferred embodiments the process is performed with the proviso that the step of recovering at least part of the water does not comprise a liquid/liquid extraction step.

In some embodiments, the process comprises the step of: purifying the recovered lactide. The step of purifying the recovered lactide is performed after the step of recovering the lactide. In some embodiments, the step of purifying the recovered lactide comprises a combination of vacuum and heating. In some embodiments, the step of purifying the recovered lactide is performed at a pressure of at most 200 mbar, for example of at most 100 mbar, for example of at least 20 mbar and at most 40 mbar, preferably of about 30 mbar. In some embodiments, the step of purifying the recovered lactide is performed at a temperature of at most the melting point of lactide, preferably of at most 90° C., for example of at least 25° C. and at most 90° C. Such processes have the advantage that less solvent is lost. Such processes also have the advantage that they provide energetic optimization. Such processes have the advantage that no solvent flaring may be required. Preferably, purification happens after separation of Lactide by filtration from decane. The separate Lactide cake contains some solvent which should be separated to produce high purity Lactide. In an alternative case, crystallization can be carried out in an static crystallizer which separates the Lactide at the end without a filtration step.

In some embodiments, the step of purifying the recovered lactide comprises a purifying crystallization step. Lactide separation and purification may also be carried out in a single static or dynamic crystallizer without filtration. Preferably, the final lactide purity is at least 98.0%, preferably at least 99.0%, preferably at least 99.5%, preferably at least 99.9%.

In some preferred embodiments, the one or more components comprise a solvent that is non-miscible with water, preferably wherein the solvent is isobutylbenzene. Such processes have the advantage of easier solvent—water separation.

Preferably, the step of converting at least part of the lactic acid into lactide and water is performed in one step. The one step process for converting lactic acid into lactide differs from the two-step synthesis in the art, in that water removal takes place during the ring-closing reaction and lactide is thus synthesized directly from aqueous lactic acid via condensation, rather than via transesterification. In some preferred embodiments, the step of converting at least part of the lactic acid into lactide and water comprises a ring-closing reaction. Preferably the conversion of lactic acid into lactide is performed in a single reactor.

When multiple reactors are used, for example at least two reactors connected in series, each reactor individually performs the one step conversion of lactic acid into lactide.

The one step conversion of lactic acid into lactide has the advantage that less side products are formed, for example LxA oligomers, such as L3A and L4A oligomers. As used herein, the term "LxA" refers to oligomer comprising x basic lactic acid units. In general, the term LxA may be used to describe the ensemble of all oligomers, wherein x is equal to or greater than 3. LxA oligomers are typically undesired in the present processes, since they are not directly converted into lactide. The one step conversion of lactic acid into lactide also has the advantage that there is less hydrolysis of lactide back into lactic acid.

Preferably, the process is an industrial process for synthesizing lactide. Preferably, the process has an output of at least 10 000 ton lactide per year, preferably at least 30 000 ton lactide per year, preferably at least 40 000 ton lactide per year, preferably at least 50 000 ton lactide per year, preferably at least 60 000 ton lactide per year, preferably at least 70 000 ton lactide per year, preferably at least 80 000 ton lactide per year.

The reactor(s) may operate in a temperature of at least 120° C., preferably at least 130° C., preferably at least 140° C., preferably at least 150° C., preferably at least 160° C., preferably at least 170° C.

In some embodiments, the at least one reactor is a mixed reactor, preferably wherein the at least one reactor is mixed mechanically and/or with internal or external fluid flow. In some preferred embodiments, the at least two reactors are mixed reactors, preferably wherein the at least two reactors are mixed mechanically and/or with internal or external fluid flow.

In some embodiments, the step of adding thermal energy to at least one of the one or more components is performed after the step of adding the at least one of the one or more components to the at least one reactor, for example by an internal exchanger or a jacketed wall. In some embodiments, the step of adding thermal energy to at least one of the one or more components is performed after the step of adding the at least one of the one or more components to the at least two reactors, for example by an internal exchanger or a jacketed wall. Internal heat exchangers may be used. The reactor may be heated by heating up the solvent entering into the reactor. A heat exchanger may be installed between two reactors.

In some embodiments, the step of recovering thermal energy is performed after the last reactor of the at least one reactor or after the last reactor of the at least two reactors. In some embodiments, the step of recovering thermal energy is performed between reactors of the at least one reactor or after the last reactor of the at least two reactors. In some embodiments, the step of recovering thermal energy is performed with a heat exchanger. Heat exchangers are preferably used to transfer the heat from the hot outlet streams to the cool inlet flows before entering into the reactor.

In some embodiments, the lactic acid is converted into lactide in a single reactor. In some embodiments, the lactic acid is independently converted into lactide in each reactor of the at least two reactors.

In some embodiments, the one or more components comprise at least one solvent. Use of a solvent may have the advantage that the lactide will be dissolved in the solvent, thereby reducing lactide hydrolysis back into lactic acid by the water. For example, in aromatic solvents, the lactide will prefer the organic phase. In some embodiments, the process comprises the step of recovering the at least one solvent, preferably the process comprises the step of recycling the at least one solvent.

An appropriate solvent may be one in which the reaction products described herein are soluble and which has an appropriate boiling point. More particularly, the boiling point preferably is sufficiently high so that at the boiling point temperature an acceptable reaction rate is achieved, but sufficiently low such that the formation of degradation products can be avoided or minimized. In some embodiments, the solvent forms a non-azeotropic mixture with water, thereby allowing the removal of water via distillation. Non-azeotropic solvents can include water immiscible aromatic solvents, water immiscible aliphatic or cyclic hydrocarbon solvents, water soluble solvents, or mixtures thereof. Water immiscible non-azeotropic solvents are preferred because, after distillation, they can be readily separated with the solvent being recycled and the water being taken out of the system. Moreover, potential byproducts obtained during the reaction process (such as water soluble short oligomers of the hydroxycarboxylic acid and/or aminocarboxylic acid) will typically dissolve in the water phase, while the cyclic esters and/or cyclic amides of interest typically remain in the organic solvent phase. This may facilitate the separation of the byproducts from the products of interest via extraction, and subsequent re-entry of the water soluble products (after hydrolysis) in the reaction process.

Solvents which are not preferred because of being potentially reactive with cyclic esters include alcohols, organic acids, esters and ethers containing alcohol, peroxide and/or acid impurities, ketones and aldehydes with a stable enol form, and amines.

Suitable solvents may include aromatic hydrocarbon solvents such as benzene, toluene, xylene, ethylbenzene, trimethylbenzene (e.g. 1,3,5-trimethylbenzene), methylethylbenzene, n-propylbenzene, isopropylbenzene, diethylbenzene, isobutylbenzene, triethylbenzene, diisopropylbenzene, n-amylnaphthalene, and trimethylbenzene; ether solvents such as ethyl ether, isopropyl ether, n-butyl ether, n-hexyl ether, 2-ethylhexyl ether, ethylene oxide, 1,2-propylene oxide, dioxolane, 4-methyldioxolane, 1,4-dioxane, dimethyldioxane, ethylene glycol diethyl ether, ethylene glycol dibutyl ether, diethylene glycol diethyl ether, diethylene glycol di-n-butyl ether, tetrahydrofuran, and 2-methyltetrahydrofuran; aliphatic hydrocarbon solvents such as n-pentane, isopentane, n-hexane, isohexane, n-heptane, isoheptane, 2,2,4-trimethylpentane, n-octane, isooctane, cyclohexane, and methylcyclohexane; and ketone solvents such as acetone, methyl ethyl ketone, methyl n-propyl ketone, methyl n-butyl ketone, diethyl ketone, methyl isobutyl ketone, methyl n-pentyl ketone, ethyl n-butyl ketone, methyl n-hexyl ketone, diisobutyl ketone, trimethylnonanone, cyclohexanone, 2-hexanone, methylcyclohexanone, 2,4-pentanedione, acetonylacetone, acetophenone, and fenchone.

In some embodiments, the at least one solvent is a $C_5$-$C_{24}$ alkane or a mixture of $C_5$-$C_{24}$ alkanes. In some embodiments, the at least one solvent is decane. Alkanes, and decane in particular, have the advantage that they can easily be separated from water, for example in a phase settler. Furthermore, they have a relatively high boiling point. Furthermore, they pose less HSE risk. Furthermore, they are stable in boiling point operating conditions. Furthermore, they are relatively cheap.

In some embodiments, the at least one solvent is benzene, preferably substituted with one or more linear or branched $C_1$-$C_4$ alkyl groups, or a mixture thereof. For example, the at least one solvent may be selected from the group comprising: isobutylbenzene, toluene, ortho-xylene, meta-xylene, para-xylene, ethylbenzene, propylbenzene, trimethylbenzene, and mixtures thereof. In some embodiments, the at least one solvent is isobutylbenzene, cumene, o-xylene or toluene, preferably isobutylbenzene. Substituted benzenes, and isobutylbenzene in particular, have the advantage that they for a better emulsion with water, and less agitation is required in the reactor(s). Furthermore, they have a relatively high boiling point. Furthermore, they provide a high yield of lactide. Furthermore, they provide a high solubility for lactide.

In some embodiments, the solvent has a standard boiling point of at least 50° C. to at most 250° C., preferably of at least 100° C. to at most 200° C., more preferably of at least 160° C. to at most 180° C. Isobutylbenzene and decane have a boiling point of about 175° C. Patent Pending™

In some embodiments, the at least one catalyst system is dispersed in the at least one reactor in form of a slurry. In some embodiments, one or more of the one or more reactors comprise a separate catalyst entry, for example wherein the separate entry comprises of at least 50 wt % catalyst, preferably 70 wt % catalyst, preferably 80 wt % catalyst.

Figure 2:
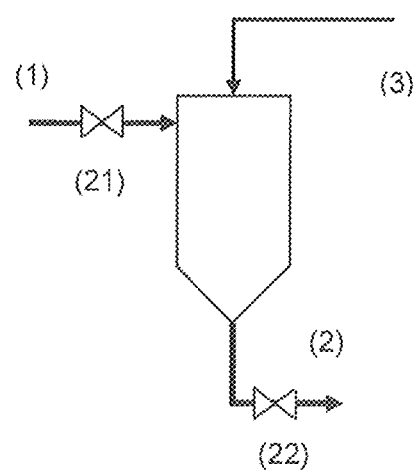
FIG. 2 illustrates a semi-batch catalyst injection system which may be used in the present invention, comprising: (1) a regenerated catalyst slurry inlet from a centrifugal separator; (2) a catalyst slurry outlet into the reactor; (3) a gas inlet to build up pressure; and (21,22) valves.

The inlet stream of the water separation unit typically contains a large content of catalysts (up to 30 wt %). This high catalyst content may be harmful for the membrane or filters used in the water separation section. In some embodiments, a catalyst separation unit may be installed upstream of this unit to protect filters/membranes. In this case a hydro-cyclone or a centrifugal separator may be used to separate catalyst and re-inject it into the reactor inlet stream or probably re-inject directly into the reactor. Direct catalyst injection into the reactor has the advantage of being able to use normal pumps on the reactor inlet stream. Preferably, a semi-batch catalyst injection systems similar to the configuration proposed in FIG. 2 is used. Two or three catalyst injection system can be installed for each reactor depending on the process configuration.

In some embodiments, the process comprises the step of recovering the at least one catalyst system, preferably recycling the at least one catalyst system. In some embodiments, the at least one catalyst system is regenerated by the solvent. In some preferred embodiments, the at least one catalyst system is regenerated by water. In some preferred embodiments, the at least one catalyst system is regenerated through calcination.

Preferably, the catalyst system comprises a zeolite catalyst. Zeolite catalysts described herein may be regenerated and reused in the process. Accordingly, particular embodiments of the process described herein may comprise a step of regenerating the zeolite catalyst. Regeneration of the zeolite catalysts can be performed via washing or calcination. Preferably, regeneration of the zeolite catalysts is done via calcination, for example at a temperature of at least 150° C. In particular embodiments, the calcination temperature is at least 200° C., for example at least 300° C., for example at least 400° C., for example about 450° C. In some embodiments, the at least one catalyst system comprises at least one acidic zeolite. The term "zeolite" as used herein refers to both natural and synthetic microporous crystalline aluminosilicate materials having a definite crystalline structure as determined by X-ray diffraction. A zeolite comprises a system of channels which may be interconnected with other channel systems or cavities such as side-pockets or cages. The channel systems may be three-dimensional, two-dimensional or one-dimensional. A zeolite comprises $SiO_4$ and $XO_4$ tetrahedra, wherein X is Al (aluminium) or B (boron). A zeolite may comprise a combination of $AlO_4$ and $BO_4$ tetrahedra. In a preferred embodiment, X is Al, and the zeolite comprises no $BO_4$ tetrahedra. The $SiO_4$ and XO4 tetrahedra are linked at their corners via a common oxygen atom. The Atlas of Zeolite Framework Types (C Baerlocher, LB McCusker, DH Olson, 6th ed. Elsevier, Amsterdam, 2007) in conjunction with the web-based version (http://www.iza-structure.org/databases/") is a compendium of topological and structural details about zeolite frameworks, including the types of ring structures present in the zeolite and the dimensions of the channels defined by each ring type. Proven recipes and good laboratory practice for the synthesis of zeolites can be found in the "Verified synthesis of zeolitic materials" 2nd Edition 2001. Various proven recipes for the synthesis comprising $BO_4$ tetrahedra are available. For example, the synthesis and characterization of boron-based zeolites having a MFI topology has been described by Cichocki and Parasiewicz-Kaczmarska (Zeolites 1990, 10, 577-582).

In some embodiments, the at least one catalyst system comprises at least one acidic zeolite comprising: two or three interconnected and non-parallel channel systems, wherein at least one of said channel systems comprises 10- or more-membered ring channels; and a framework $Si/X_2$ ratio of at least 24 as measured by NMR; or three interconnected and non-parallel channel systems, wherein at least two of said channel systems comprise 10- or more-membered ring channels; and a framework $Si/X_2$ ratio of at least 6 as measured by NMR; wherein each X is Al or B.

As used herein, the term "channel system" refers to a system of parallel and crystallographically equivalent channels, wherein the channels are 8-membered ring channels or larger, for example wherein the channels are 10-membered ring channels or 12-membered ring channels. Accordingly, as used herein, the term "channel" refers to an 8- or more membered ring channel which is part of a system of parallel and crystallographically equivalent channels.

Preferred zeolites for use in the present process comprise 10- or more-membered ring channels, such as 10-membered ring channels (10MR), 12-membered ring channels (12MR), or larger. The ring size for each known zeolite framework type is provided in the Atlas of Zeolite Framework Types (C Baerlocher, LB McCusker, DH Olson, 6th ed. Elsevier, Amsterdam, 2007), which is incorporated herein by reference.

As used herein the terms "8-membered ring channels" or "8MR" refer to a channel comprising unobstructed 8-membered rings, wherein the 8-membered rings define the smallest diameter of the channel. An 8-membered ring comprises 8 T atoms, and 8 alternating oxygen atoms (forming the ring), wherein each T is Si, Al or B. As used herein the terms "10-membered ring channels" or "10MR" refers to a channel comprising unobstructed 10-membered rings, wherein the 10-membered rings define the smallest diameter of the channel. A 10-membered ring comprises 10 T atoms, and 10 alternating oxygen atoms (forming the ring), wherein each T is Si, Al or B. As used herein the terms "12-membered ring channels" or "12MR" refers to a channel comprising unobstructed 12-membered rings, wherein the 12-membered rings define the smallest diameter of the channel. A 12-membered ring comprises 12 T atoms, and 12 alternating oxygen atoms (forming the ring), wherein each T is Si, Al or B. As used herein, the term "10-or-more-membered ring channel" refers to a 10-membered ring channel or larger, and therefore comprises for example both 10-membered ring channels and 12-membered ring channels.

The framework $Si/X_2$ ratio may be determined via Nuclear Magnetic Resonance (NMR) measurements, more particularly 29Si and 27Al NMR. In some embodiments, X is Al. In a preferred embodiment, there is no framework B, and the $Si/X_2$ ratio is equal to the $Si/Al_2$ ratio. The determination of the $Si/Al_2$ ratio by NMR may be performed as described by Klinowski (Ann. Rev. Mater. Sci. 1988, 18, 189-218); or as described by G. Engelhardt and D. Michel (High-Resolution Solid-State NMR of Silicates and Zeolites. John Wiley & Sons, Chichester 1987. xiv, 485 pp). The determination of the $Si/B_2$ ratio by NMR may be performed as discussed by D. Trong On et al. (Studies in Surface Science and Catalysis 1995, 97, 535-541; Journal of Catalysis, November 1995, Volume 157, Issue 1, Pages 235-243).

The preferred zeolites used in the process described herein may comprise $AlO_4$ tetrahedra, $BO_4$ tetrahedra, or both. Accordingly, in some embodiments, $X_2$ is $(Al_2+B_2)$. Thus, for a given zeolite, the $Si/X_2$ framework ratio remains the same upon substitution of framework Al by B, or vice versa. However, it is envisaged that in particular embodiments, the zeolites may not comprise $BO_4$ tetrahedra, or an insignificant amount thereof (e.g. an Al/B ratio of 100 or more). Thus, in particular embodiments, $X_2$ may be $Al_2$. The $Si/X_2$ ratios referred to herein are molar ratios as determined via NMR, unless specified otherwise. It will be understood by the skilled person that the Si/X2 ratio referred to herein is equal to the $SiO_2/X_2O_3$ molar ratio, wherein $X_2O_3$ is ($Al_2O_3$ and/or $B_2O_3$). Moreover, the skilled person will understand that by dividing the $Si/X_2$ ratio by two, the Si/X molar ratio is obtained, wherein X is (Al and/or B).

Accordingly, in some embodiments, the zeolite(s) for use in the process described herein may comprise a framework $Si/X_2$ ratio of at least 24, for example a framework $Si/Al_2$ ratio of at least 24, wherein the zeolite further comprises at least two interconnected and non-parallel channel systems wherein at least one of the interconnected and non-parallel channel systems comprises 10- or more-membered ring channels, i.e. at least one of the channel systems comprises 10- or more-membered ring channels, and at least one other channel system comprises 8- or more-membered ring channels. Examples of such zeolites are zeolites comprising a topology selected from the group comprising FER, MFI, and MWW.

In some embodiments, both of the at least two channel systems comprise 10- or more-membered ring channels. In some embodiments, at least one of the channel systems comprises 12- or more-membered ring channels.

In some embodiments, the zeolite for use in the process described herein may comprise a framework $Si/X_2$ ratio of at least 6, for example a framework $Si/Al_2$ ratio of at least 6; wherein the zeolite further comprises three interconnected and non-parallel channel systems wherein at least two of the interconnected and non-parallel channel systems comprise 10- or more-membered ring channels, i.e. at least two of the channel systems comprise 10- or more-membered ring channels, and the other channel system comprises 8- or more-membered ring channels. Examples of such zeolites include, but are not limited to zeolites comprising a topology selected from the group comprising BEA, FAU, and MEL.

In some embodiments, the three channel systems all comprise 10- or more-membered ring channels. In particular embodiments, at least one of the channel systems comprises 12- or more-membered channels.

In some embodiments, at least two of the channel systems comprise 12- or more-membered ring channels. Examples of such zeolites include, but are not limited to zeolites comprising a topology selected from the group comprising BEA and FAU.

Preferably, the channels defined by the zeolite topology are large enough to be accessible for the lactic acid monomers, but small enough to prevent significant formation and/or diffusion of trimers or higher order oligomers. Accordingly, in some embodiments, the zeolite only comprises channels with a ring size of at most 18, preferably of at most 14, for example of at most 12.

In some embodiments, the zeolite for use in the process described herein comprises a topology selected from the group comprising: BEA, MFI, FAU, MEL, FER, and MWW. These zeolites provide a particularly high selectivity towards lactide. In certain embodiments, the zeolite(s) comprise a topology selected from the group consisting of BEA, MFI, FAU, and MWW. In specific embodiments, the zeolite(s) comprise a zeolite with a BEA topology. In some embodiments, the acidic zeolite comprises a topology selected from the group comprising BEA, MFI, FAU, MEL, FER, and MWW, preferably BEA. In some embodiments, the at least one catalyst system comprises an acidic zeolite, preferably wherein the at least one catalyst system comprises an H-BEA zeolite. Exemplary commercially available zeolites suitable for use in the processes described herein include, but are not limited to, Beta polymorph A (BEA topology), ZSM-5 (Mobil; MFI topology), Y zeolite (FAU topology), and MCM-22 (Mobil; MWW topology).

In some embodiments, the zeolite comprises channels having an average (equivalent) diameter of at least 4.5 Å. More particularly, the zeolite may comprise two or more non-parallel channels having an average diameter of at least 4.5 Å. The channel diameter may be determined theoretically via knowledge of the zeolite framework type, or via x-ray diffraction (XRD) measurements, as will be known by the skilled person. Preferably, the zeolite comprises two or more non-parallel and interconnected channels having an average (equivalent) diameter between 4.5 and 13.0 Å, more preferably between 4.5 and 8.5 Å. Preferably, the diameter for the appropriate topology is obtained from international standard literature: the Atlas of Zeolite structures or the corresponding online database, found at http://www.iza-structure.org/databases/, as referenced above. The (equivalent) diameter of the channels may also be determined experimentally via N2 adsorption, for example as discussed by Groen et al. (Microporous and Mesoporous Materials 2003, 60, 1-17), Storck et al. (Applied Catalysis A: General 1998, 174, 137-146) and Rouquerol et al. (Rouquerol F, Rouquerol J and Sing K, Adsorption by powders and porous solids: principles, methodology and applications, Academic Press, London, 1999).

In some embodiments, the zeolite may further comprise mesopores. The presence of mesopores may increase the accessibility of the lactic acid to the micropores, and may therefore further increase the reaction speed. However, it is also envisaged that the zeolite may not comprise mesopores. As used herein the term "mesopores" refers to pores in the zeolite crystal having average diameters of 2.0 nm to 50 nm. For pore shapes deviating from the cylinder, the above ranges of diameter of mesopores refer to equivalent cylindrical pores. The mesopore average diameter may be determined by gas sorption techniques such as $N_2$ adsorption.

The zeolite(s) may be used as such, for example as a powder. In certain embodiments, the zeolite(s) may be formulated into a catalyst by combining with other materials that provide additional hardness or catalytic activity to the finished catalyst product. Materials which can be blended with the zeolite may be various inert or catalytically active materials, or various binder materials. These materials include compositions such as kaolin and other clays, phosphates, alumina or alumina sol, titania, metal oxide such as zirconia, quartz, silica or silica sol, metal silicates, and mixtures thereof. These components are effective in densifying the catalyst and increasing the strength of the formulated catalyst. Various forms of rare earth metals can also be added to the catalyst formulation. The catalyst may be formulated into pellets, spheres, extruded into other shapes, or formed into spray-dried particles. The amount of zeolite which is contained in the final catalyst product may range from 0.5 to 99.9 weight %, preferably from 2.5 to 99.5 weight % of the total catalyst, preferably from 2.5 to 95 weight %, preferably from 2.5 to 90 weight % of the total catalyst, most preferably from 2.5 to 80 weight %; for example from 20 to 95 weight %, preferably from 20 to 90 weight %, most preferably from 20 to 80 weight %, with weight % based on the total weight of catalyst product.

In some embodiments, the zeolite(s) for use in the processes described herein can be exposed to a (post-synthesis) treatment to increase the $Si/X_2$ framework ratio. Methods to increase the $Si/Al_2$ ratio of zeolites are known in the art, and include dealumination of the framework via (hydro)thermal treatment, extraction of framework aluminum with acid, and replacement of framework aluminum with silicon by reaction with silicon halides or hexafluorosilicates. An exemplary method of dealumination is described by Remy et al. (J. Phys. Chem. 1996, 100, 12440-12447; hereby incorporated by reference).

The zeolites for use in the process described herein preferably are Brønsted acidic zeolites, i.e. having proton donating sites in the micropores. In some embodiments, the zeolite has a Brønsted acid density between 0.05 and 6.5 mmol/g dry weight. When all Al T-sites are counterbalanced with an acidic proton (as opposed to a cation), the Brønsted acid density can be directly derived from the $Si/Al_2$ ratio, for example as discussed in the Handbook of Heterogeneous Catalysis, second edition, edited by G. Ertl, H. Knözinger, F. Schüth and J. Weitkamp, Wiley 2008.

The zeolites for use in the processes described herein can be obtained in acidic form (acidic H-form zeolite) or (partly) exchanged with a cation other than $H^+$. In some embodiments, the acidic H-form zeolites can be used as such. In some other embodiments, the zeolites for use in the processes described herein can be exposed to a (post-synthesis) treatment to increase the Brønsted acid density.

Brønsted acid sites in zeolites can be readily generated by aqueous ion exchange with an ammonium salt, followed by thermal decomposition of the ammonium ions inside the zeolite. Alternatively, the acid sites may be generated by aqueous ion exchange with the salt of a multivalent metal cation (such as $Mg^{2+}$, Ca2+, $La^{3+}$, or mixed rare-earth cations), followed by thermal dehydration (J. Weitkamp, Solid State Ionics 2000, 131, 175-188; hereby incorporated by reference). In some embodiments, the acidic zeolite has a Brønsted acid density between 0.05 and 6.5 mmol/g dry weight.

In some embodiments, the process is performed in the absence of any catalyst system. Such processes may have up to 25-40% lower conversion and lower yield. However, such processes have the advantage that they can work at lower capacity and lower cost. Such processes have the advantage that they can work with higher recirculation. Such processes have the advantage that separation is easier.

In some embodiments, the process is sometimes performed in the presence of at least one catalyst system and sometimes performed in the absence of any catalyst system. The choice may be made depending on a variety of factors, including the composition of the feed. This demonstrates the high versatility of such a process.

In some embodiments, at least part of the catalyst system is recovered, preferably together with at least part of the water, preferably through a decantation step. Alternatively, the catalyst system may be recovered through filtration, centrifugal separation or with a hydrocyclone.

In some embodiment, at least part of the catalyst system is present in the recovered solvent. The catalyst system may be separated from the solvent by the methods described above.

In some embodiments, the process comprises the step of recovering at least part of the water, optionally wherein the water comprises at least part of the at least one catalyst system.

In some embodiments, the step of recovering at least part of the water comprises a filtration step preferably membrane filtration, for example through reverse osmosis. In some embodiments, the step of recovering at least part of the water comprises a distillation step. In some embodiments, the step of recovering at least part of the water comprises reactive distillation. In some embodiments, the step of recovering at least part of the water comprises reactive distillation. In some embodiments, the step of recovering at least part of the water comprises divided wall column distillation. Distillation plates may be provided on top of the reactor(s). Fluid heating may be provided by a reboiler, preferably placed at the bottom of the reactor(s).

In some embodiments, the step of recovering thermal energy is performed after the step of recovering at least part of the water.

The lactic acid may be produced industrially via bacterial fermentation of glucose or sucrose. Microbial fermentation generally results in L-lactic acid, which restricts the potential of PLA, as superior stereocomplexes PLLA/PDLA require a source of D-lactic acid. In some embodiments, the lactic acid is obtained by bacterial fermentation of glucose or sucrose.

Alternatively, chemocatalytic transformation of trioses, hexoses, cellulose, or glycerol, may result in lactic acid obtained as a racemic mixture. In some preferred embodiments, the lactic acid is obtained by chemocatalytic transformation of trioses, hexoses, cellulose, or glycerol.

In some embodiments, the lactic acid comprises L-lactic acid. In some preferred embodiments, the lactic acid comprises D-lactic acid. In some embodiments, the lactic acid comprises at least 90% by weight, for example at least 95% by weight, for example at least 98% by weight, for example at least 99% by weight L-lactic acid.

In some embodiments, the one or more components provided to the at least one reactor comprises at least 3% by weight of water and at most 95% by weight of water, with % by weight based on the total weight of the one or more components, preferably at least 5% by weight and at most 50% by weight, with % by weight based on the total weight of the one or more components provided to the at least one reactor, preferably at least 10% by weight and at most 30% by weight, with % by weight based on the total weight of the one or more components provided to the at least one reactor.

In some embodiments, the one or more components provided to the at least one reactor at least 90% by weight of solvent, with % by weight based on the total weight of the one or more components, preferably at least 95% by weight, preferably at least 99.5% by weight.

In some embodiments, the mass flow rate of total quantity of solvent provided to all reactors is at least 4 times to at most 30 times the mass of lactic acid provided to all reactors, preferably at least 6 times to at most 25 times, preferably at least 9 to at most 20 times.

In some embodiments, the one or more components provided to the at least one reactor comprises at least 1% by weight of catalyst system and at most 25% by weight of catalyst system, with % by weight based on the total weight of the one or more components, preferably at least 3% by weight and at most 10% by weight, with % by weight based on the total weight of the one or more components provided to the at least one reactor.

In some embodiments, the one or more components provided to the at least one reactor comprises at most 1.00% by weight of organic acids other than lactic acid, preferably at most 0.10% by weight, preferably at most 0.01% by weight, with % by weight based on the total weight of the one or more components provided to the at least one reactor.

Lactide has two asymmetric carbon atoms so it may be obtained in three stereoisomeric forms: L-L-lactide in which both asymmetric carbon atoms possess the L (or S) configuration; D-D-lactide in which both asymmetric carbon atoms possess the D (or R) configuration; and meso-lactide (D-L-lactide) in which one asymmetric carbon atom has the L-configuration and the other has the D-configuration.

In some embodiments of the processes described herein, the hydroxycarboxylic acid is L-lactic acid (with an enantiomeric excess of at least 90%, preferably at least 95%, more preferably at least 98%) and the corresponding cyclic ester is L-L-lactide.

In some embodiments of the processes described herein, the hydroxycarboxylic acid is D-lactic acid (with an enantiomeric excess of at least 90%, preferably of at least 95%, more preferably of at least 98%) and the corresponding cyclic ester is D-D-lactide.

In some embodiments, the step of recovering at least part of the thermal energy is performed prior to the step of purifying the recovered lactide. In some embodiments, the step of recovering at least part of the thermal energy is performed prior to the purifying crystallization step.

In some embodiments, the step of recovering at least part of the thermal energy is performed during the step of purifying the recovered lactide. In some embodiments, the step of recovering at least part of the thermal energy is performed during the purifying crystallization step.

In some embodiments, the step of purifying the recovered lactide comprises a solvent-solvent extraction step. In some embodiments, the step of purifying the recovered lactide comprises a filtration step, preferably through a membrane. Such processes have the advantage that high quality water is produced.

The filtration is preferably for separation of solid Lactide from the crystallization step. This filtration may be replaced by a crystallization system that separates the solids without a filter such as a static crystallizer in which lactide crystallizes over the walls of the crystallizer. The purification step occurs typically after the filtration step (or after the crystallization if filtration is not used). The purpose is to remove the trace of solvent present in the separated lactide to produce high purity Lactide, for example of at least above 99%, preferably of at least 99.9%, preferably of at least 99.99%. In this step a solvent/solvent extraction may be used but not preferred. Instead a vacuum flash can be used to evaporate the solvent in low pressure and temperatures just below the melting point of Lactide as written in the previous sections.

In some embodiments, the process has a lactide yield of at least 60%, preferably at least 65%, preferably at least 70%, preferably at least 75%, preferably at least 80%, preferably at least 85%.

In some preferred embodiments, the process further comprises the step of: converting at least part of the recovered lactide into polylactic acid (PLA), preferably PLLA.

The advantages of the present invention are illustrated by the following examples.

EXAMPLES

Example 1

This example illustrates a process for synthesizing lactide from lactic acid according to a combination of embodiments of the present invention. Reference is made to FIG. 1, composed of FIG. 1A, FIG. 1B, FIG. 1C, and FIG. 1D, which represents a flow diagram of the process of Example 1.

An original feed (100) is provided, wherein the original feed (100) comprises lactic acid (110). When the lactic acid has been obtained from a bio-based feedstock, the original feed (100) usually also comprises lactic acid dimer (120), lactic acid oligomers (130), and water (140). Flow circulation of the components may be performed by one or more pumps (101, 102, 103, 104).

A solvent make-up (150) is provided separately. A catalyst system (160) is present in a closed cycle. A catalyst makeup may be provided to replace the deactivated catalyst. This catalyst makeup may be added directly to first reactor or be injected into the feed line or be injected with fresh feed.

The components of the feed (110, 120, 130, 140), and optionally the catalyst system (160), are provided to a first reactor (710) suitable for one-step lactide formation. The solvent (150) is provided separately to the first reactor (710). The mixture exiting the first reactor is provided to a second reactor (720) suitable for one-step lactide formation.

The components of the feed (110, 120, 130, 140) are optionally heated by a steam generator (500), which generates heated steam (511) that passes heat onto the components of the feed (110, 120, 130, 140) through a heat exchanger (510). The resulting cooled steam or condensed water (512) may then be heated again by the steam generator (500) The solvent is heated, for example by the steam generator (500), which generates heated steam (521) that passes heat onto the components of the solvent (150) through a heat exchanger (520). The resulting cooled steam or condensed water (522) may then be heated again by the steam generator (500).

The original feed (100) may be combined with water (140), and optionally with lactic acid oligomers (130) and/or the catalyst system (160), that was recovered from the mixtures exiting the first reactor (710) and the second reactor (720), to obtain a mixture. This water (140), together with water (140) from the original feed (100), may be used to hydrolyze the lactic acid oligomers (130) (obtained from either reactor (710, 720) or already present in the original feed (100)) into lactic acid (100) and lactic acid dimer (120) in the recycling pipes. This water (140), together with water (140) from the original feed (100), may also be used to regenerate the catalyst system (160) (present in a closed cycle) in the recycling pipes. Optionally a separate recycling reactor (730) is provided.

Water (140) separation, optionally wherein the water (140) comprises lactic acid oligomers (130) and/or the catalyst system (160), can occur between reactors (410), as a decantation step (420) (or alternatively by distillation or centrifugation) after the second reactor (720). The mixture then is sent to a water separation membrane (430) after mixing with the original feed (100). These steps result in high quality water (400) and a mixture with adjusted water concentration to be sent to the reactor. The outlet stream from the decantation step containing water may have some LA and L2A due to possible hydrolysis of the oligomers inside the decanter.

From the mixture exiting the second reactor (720), the water (140), optionally comprising lactic acid oligomers (130) and/or the catalyst system (160), is separated from the lactide (200) and the solvent (150) in a decantation step (420).

The lactide (200) and solvent (150) are further separated using an optional refrigeration cycle for lactide crystallization (300). The cooling may be carried out by refrigeration as in this example, or simply by cooling water. The refrigeration cycle for lactide crystallization (300) preferably comprises a compressor (310), heat exchangers for the refrigeration cycle (311, 312), and a valve for refrigeration cycle (315).

Preferably, the lactide crystallization occurs in two steps: lactide (200) crystallization in a first crystallization reactor (301) (optionally with heat recovery) and lactide (200) crystallization in a second crystallization reactor (302) to finish the crystallization.

The lactide (200) is subsequently separated from the solvent (150) using a lactide filter (210). Further purification of the lactide (200) may be performed with a valve for lactide purification (215) and a lactide purifier (220).

Energy optimization is provided with multiple heat recovery steps (selected temperatures are shown in FIG. 1). A first heat recovery step (610) recovers thermal energy from the lactide (200) and the solvent (150) exiting the second reactor through a heat exchanger (611), and provides the thermal energy to the solvent (150) through a heat exchanger (612). A second heat recovery step (620) recovers thermal energy from the water (140), and optionally the lactic acid oligomers (130) and/or catalyst system (160), exiting the first and/or second reactor through a heat exchanger (621), and provides the thermal energy to the solvent (150) through a heat exchanger (622). A third heat recovery step (630) recovers thermal energy from the lactide (200) and the solvent (150) during a crystallization step (301), and provides the thermal energy to the solvent (150) through a heat exchanger (632).

This example permits to produce 7.29 ton/h of lactide and 2.84 ton/h of water with an inlet feed flow rate of 10.12 ton/h.

The inlet flow comprises 90% by weight of lactic acid equivalents and apparent 10% by weight of water. The lactic acid equivalents itself, comprises approximately 70% by weight of lactic acid, 23% by weight of lactic acid dimers and 7% by weight of lactic acid trimers, the % by weight based on the total weight of the lactic acid equivalents. Where relevant, the amounts of heat that are to be added to the process or are liberated during the process are mentioned in FIG. 1 (as Q=...), the unit used for these amounts of heat is kJ/sec. During the two crystallization steps, 2200 kWh can be recovered, which corresponds to about 20% of the total recovered energy during the process. This also requires 50% less cooling capacity in the refrigeration cycle.

Example 2

FIG. 2 illustrates a semi-batch catalyst injection system which may be used in the present invention.

The inlet stream of the water separation unit typically contains a large content of catalysts (up to 30 wt %). This high catalyst content may be harmful for the membrane or filters used in the water separation section. In this case, a catalyst separation unit may be installed upstream of this unit to protect filters/membranes. In this case, a hydrocyclone or a centrifugal separator may be used to separate catalyst and re-inject it into the reactor inlet stream or probably re-inject directly into the reactor. Direct catalyst injection into the reactor has the advantage of being able to use normal pumps on the reactor inlet stream.

The catalyst injection into the reactor may require a dedicated system particularly in the case of a pressurized reactor. A possible method is use of semi-batch catalyst injection systems similar to the configuration proposed in FIG. 2 This system operates in three phases: Storage: during which valve (22) is closed and the system receives catalysts from stream (1) from the centrifugal separator—Pressurization: in this phase the catalyst inlet is stopped by closing valve (21) and the system is put under pressure via gas inlet line (3)—Discharge: catalysts are discharged into the reactor during this phase by partially opening the valve (22).

Two or three catalyst injection system can be installed for each reactor depending on the process configuration.

Example 3

The role of solvent is to avoid direct contact between water and produced lactide. However, water presence may have positive impact via hydrolysis of oligomers. In case the solvent has a good solubility for lactide and little solubility for water, it should be less harmful for lactide in the reactor. However, water presence may cause lactide hydrolysis if solvent does not dissolve well produced lactide. This depends on the overall reaction and dissolution mechanism.

Some alternative designs are proposed in this example to add a distillation option directly into the reactor for in situ water separation. Various kinds of reactive distillation reactors may be used in this case. FIG. 3 shows some possible configurations. Depending on the nature of the solvent, other kind of designs may be used. Some advanced distillation systems such as divided wall column may be used to produce a concentrated lactide outlet stream inside the reactor to ease the downstream separation steps. The energy consumption may be reduced by use of heat integration to recover at least a part of the evaporation energy which is inherent to the distillation.

Example 4

Figure 4:
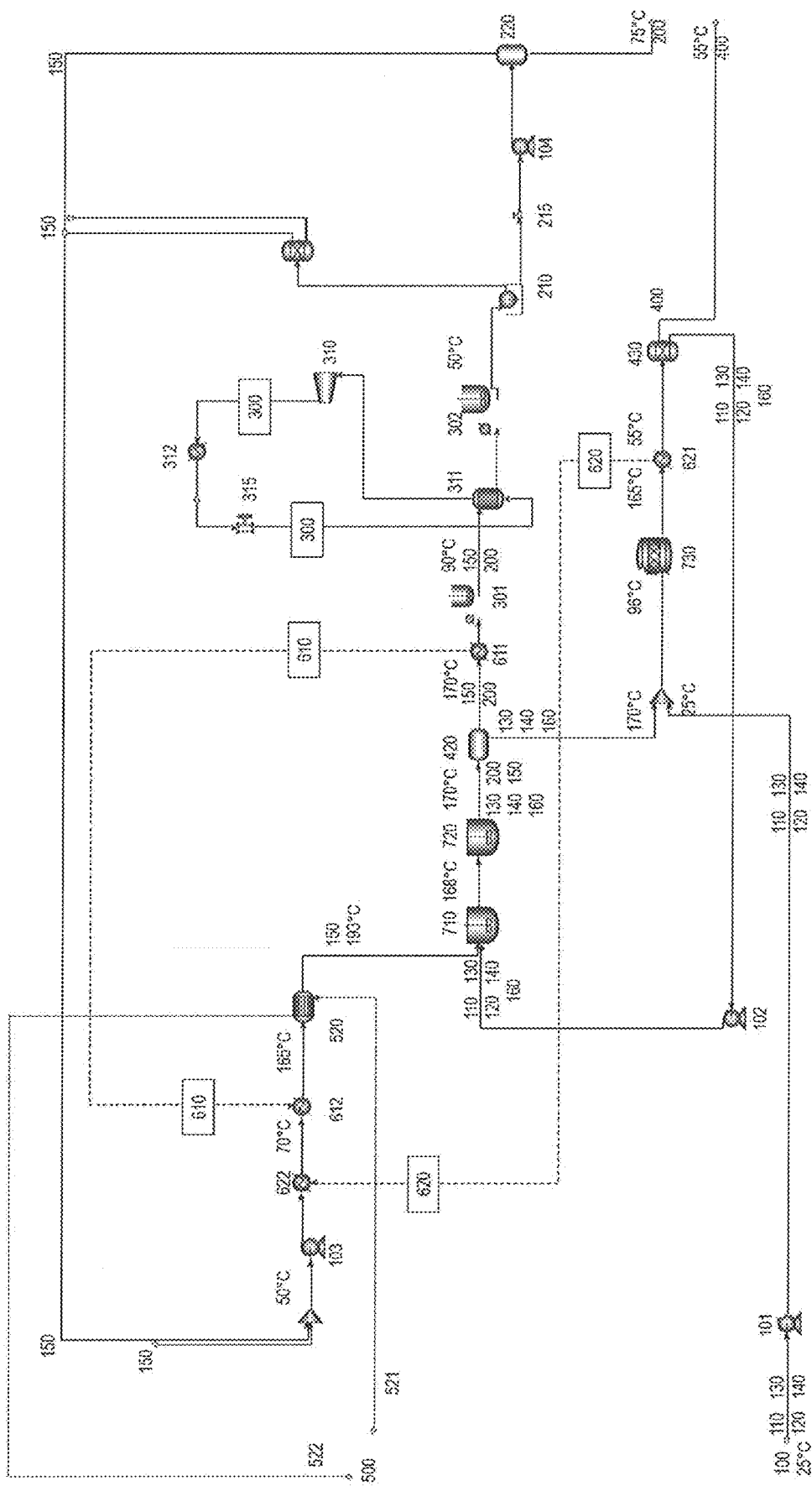
FIG. 4 represents a flow diagram of a process, combining several preferred embodiments of the present invention.

This example illustrates a process for synthesizing lactide from lactic acid according to a combination of embodiments of the present invention. Reference is made to FIG. 4, which represents a flow diagram of the process of Example 4._All the thermal energy is added via the solvent stream, further reducing the CAPEX compared to Example 1.

An original feed (100) is provided, wherein the original feed (100) comprises lactic acid (110). When the lactic acid has been obtained from a bio-based feedstock, the original feed (100) usually also comprises lactic acid dimer (120), lactic acid oligomers (130), and water (140). Flow circulation of the components may be performed by one or more pumps (101, 102, 103, 104).

A solvent make-up (150) is provided separately. A catalyst system (160) is present in a closed cycle. A catalyst makeup may be provided to replace the deactivated catalyst. This catalyst makeup may be added directly to first reactor or be injected into the feed line or be injected with fresh feed.

The components of the feed (110, 120, 130, 140), and optionally the catalyst system (160), are provided to a first reactor (710) suitable for one-step lactide formation. The solvent (150) is provided separately to the first reactor (710). The mixture exiting the first reactor is provided to a second reactor (720) suitable for one-step lactide formation.

The solvent is heated, for example by the steam generator (500), which generates heated steam (521) that passes heat onto the components of the solvent (150) through a heat exchanger (520). The resulting cooled steam or condensed water (522) may then be heated again by the steam generator (500).

The original feed (100) may be combined with water (140), and optionally with lactic acid oligomers (130) and/or the catalyst system (160), that was recovered from the mixtures exiting the second reactor (720), to obtain a mixture. This water (140), together with water (140) from the original feed (100), may be used to hydrolyze the lactic acid oligomers (130) (obtained from either reactor (710, 720) or already present in the original feed (100)) into lactic acid (100) and lactic acid dimer (120) in the recycling pipes. This water (140), together with water (140) from the original feed (100), may also be used to regenerate the catalyst system (160) (present in a closed cycle) in the recycling pipes. Optionally a separate recycling reactor (730) is provided.

Water (140) separation, optionally wherein the water (140) comprises lactic acid oligomers (130) and/or the catalyst system (160), may be performed as a decantation step (420) (or alternatively by distillation or centrifugation) after the second reactor (720). The mixture then is sent to a water separation membrane (430) after mixing with the original feed (100) and optionally passing through the recycling reactor (730).

These steps result in high quality water (400) and a mixture with adjusted water concentration to be sent to the reactor. The outlet stream from the decantation step containing water may have some LA and L2A due to possible hydrolysis of the oligomers inside the decanter.

From the mixture exiting the second reactor (720), the water (140), optionally comprising lactic acid oligomers (130) and/or the catalyst system (160), is separated from the lactide (200) and the solvent (150) in a decantation step (420).

The lactide (200) and solvent (150) are further separated using an optional refrigeration cycle for lactide crystallization (300). The cooling may be carried out by refrigeration as in this example, or simply by cooling water. The refrigeration cycle for lactide crystallization (300) preferably comprises a compressor (310), heat exchangers for the refrigeration cycle (311, 312), and a valve for refrigeration cycle (315).

Preferably, the lactide crystallization occurs in two steps: lactide (200) crystallization in a first crystallization reactor (301) (optionally with heat recovery) and lactide (200) crystallization in a second crystallization reactor (302) to finish the crystallization.

The lactide (200) is subsequently separated from the solvent (150) using a lactide filter (210). Further purification of the lactide (200) may be performed with a valve for lactide purification (215) and a lactide purifier (220).

Energy optimization is provided with multiple heat recovery steps (selected temperatures are shown in FIG. 4). A first heat recovery step (610) recovers thermal energy from the lactide (200) and the solvent (150) exiting the second reactor through a heat exchanger (611), and provides the thermal energy to the solvent (150) through a heat exchanger (612). A second heat recovery step (620) recovers thermal energy from the water (140), and optionally the lactic acid oligomers (130) and/or catalyst system (160), exiting the first and/or second reactor through a heat exchanger (621), and provides the thermal energy to the solvent (150) through a heat exchanger (622).

Compared to Example 5, the above feed (100) is injected into the separated water stream from the decantation step (420). Accordingly, the feed (100) is heated up to 96° C. due to direct mixing without use of heat exchanger. This causes the lactic acid oligomers that are present in the feed to hydrolyze to LA and L2A. Also, the feed has to pass through water separation membrane (430) reducing the water content that is fed into the reactor. Therefore, the recirculation rate is reduced by about 20%. The heating rate is considerably reduced due to substitution of the energy intensive distillation unit. Due to heat integration and substitution of the distillation unit, the total heat required in this example is about 25% of the requirement in the Example 5. In addition, the maximum temperature of the streams containing lactide (200) in this example is limited to 168° C. which permits avoiding thermal degradation of LD.

Example 5

Figure 5:
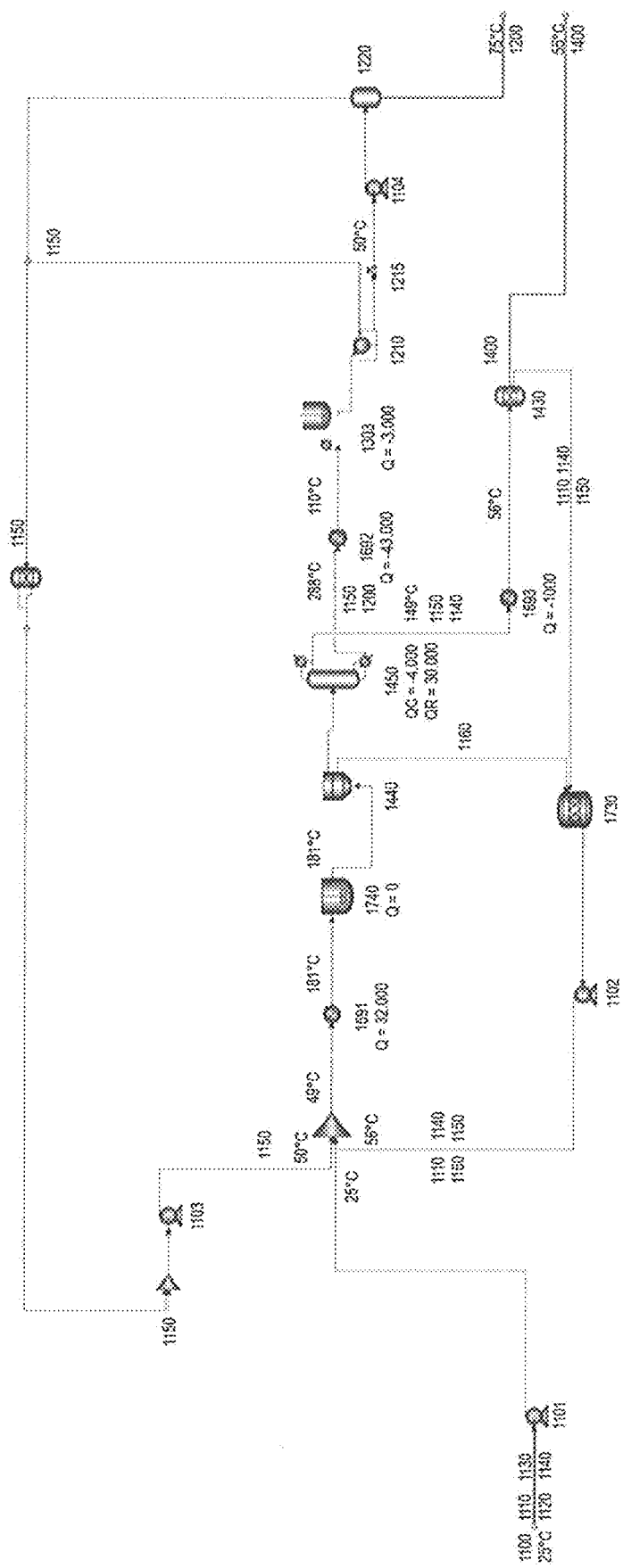
FIG. 5 represents a flow diagram of a process suitable to produce lactide, using distillation in the purification steps.

This example illustrates a process for synthesizing lactide from lactic acid. Reference is made to FIG. 5, which represents a flow diagram of the process of Example 5.

An original feed (1100) is provided, wherein the original feed (1100) comprises about 10% by weight of water (1140) and about 90% by weight lactic acid equivalent, itself comprising lactic acid (1110), lactic acid dimer (1120), lactic acid oligomers (1130). Flow circulation of the components is be performed by one or more pumps (1101, 1102, 1103, 1104). A catalyst system (1160) is present in a closed cycle.

The components of the feed (1110, 1120, 1130, 1140), the catalyst system (1160), an d the solvent (1150) are mixed and heated up in a first heat exchanger (1691) before these components enter the reactor (1740) suitable for one-step lactide formation. After a residence time of 1 hour in the reactor (1740), the reaction products leave the reactor (1740) and the solids (comprising the catalyst (1160) are separated from the rest of the reaction mixture by centrifuge (1440). Said solids are sent to a recycling reactor (1730). The liquid fraction is fed into a distillation column (1450), wherein the heavy fraction is separated from the light fraction. The light fraction comprises solvent (1150), (decane in this case) that form an azeotrope with water (1140). This light fraction is send through a heat exchanger (1693) to be cooled down and water (1400) is separated from light fraction. The heavy fraction does comprise lactide (1200), lactic acid dimer (1120) and lactic acid oligomer (1130).

The heavy fraction is passed through a heat exchanger (1692) to cool it down, before it is crystallized in crystallization reactor (1303) and filtered by filter (1210). The filtrate is reused as solvent (1150) and carries the lactic acid dimers (1120) and lactic acid oligomers (1130) back into the reactor. The solid fraction is further purified in lactide purifier (1220) to yield the desired lactide (1200). An optional regeneration step may be added into the solvent and feed stream to regenerate lactic acid oligomers (1130) and lactic acid dimers (1120) by hydrolysis with water before mixing with catalyst stream.

This example permits to produce 7.18 ton/h of lactide and 2.83 ton/h of water with an inlet feed flow rate of 10.12 ton/h. Where relevant, the amounts of heat that are to be added to the process or are liberated during the process are mentioned in FIG. 5 (as Q= . . . ), wherein QC stands for the "cooling heat rate" and QR stands for the reboiler heat rate. The unit used for these amounts of heat is kJ/sec.

The distillation column in this example requires large amounts of energy, namely 30 MJ/s. Not all the lactic acid oligomers are being removed from the heavy fraction. This requires extra efforts during the purification of the lactide and it makes the recirculation system of the light fraction less effective to turn the oligomers into useful starting materials for the lactide formation. Further, there is a reboiler needed that warms up the heavy fraction comprising the lactide (1200) to about 288° C. This causes partial degradation of the formed lactide (1200), negatively influencing the yield of the overall process. All this can lead to about 20% higher energy consumption than in the process of Example 1.

Another disadvantage of this set up is that the feed is added just before the reactor, whereas the feed in Example 1 and Example 4 is added in the water recycling loop. The feed in example 1 and 4 has to pass through recycling reactor (730) before it enters the reactor (710). This has the advantage that even before the feed enters the reaction, the oligomers that are present in the feed are getting broken down to LA or L2A, and enter the reactor (710) as useful starting material. If the feed is added directly to the reactor, the oligomers cannot take part in the reaction and are only be able to be processed after they passed through a cracking step. Overall this lowers the efficiency of the overall lactide formation.

Example 6

Figure 6:
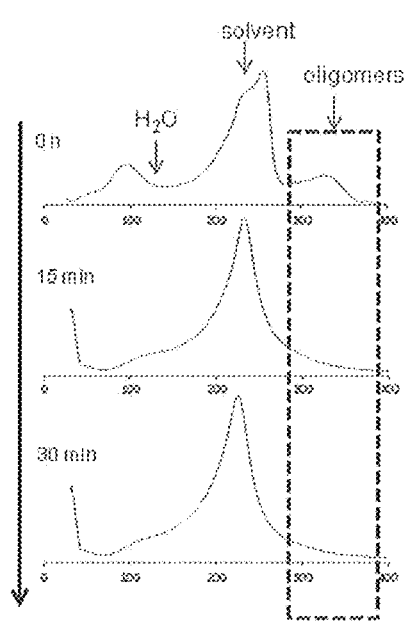
FIG. 6 shows the regeneration in water of 45° C. of a solid catalyst suitable to be used in the formation of lactide in some embodiments of the invention.

The catalyst leaves the reactor with a certain amount of lactic acid oligomers adhering on the surface of the catalyst. FIG. 6 shows thermogravimetric analysis (TGA) of used catalyst particles after no regeneration, after 15 minutes of regeneration and after 30 minutes of regeneration in water at 45° C. The first graph (0 h) of the figure shows the TGA results carry out on a non-generated catalyst comprising oligomers on the surface. Three peaks can be distinguished in this case, the first peak (around 100° C.) corresponds the removal of water, the second peak (between 200° C. and 300° C. corresponds to the removal of solvent, and the third peak (between 300° C. and 370° C. corresponds to the removal of oligomers from the catalyst surface. The second graph (15 min) shows the TGA results for the same catalyst comprising oligomers on the surface after 15 min contact with water of 45° C. to hydrolyze oligomers and regenerate catalyst. In this case, the third peak related to the oligomer does not appear, showing that the contact with water has completely removed oligomers and regenerated the catalyst. The third graph show the TGA results for the same catalyst comprising oligomers on the surface after contact with water of 45° C. for 30 min. The TGA results are approximately identical to the TGA results after 15 min water exposure. These results show that catalyst can be effectively regenerated by water in a contact time below 15 min.

Contact time may be reduced if the water temperature is higher than 45° C. as shown in examples 1 and 4 where the separated water and catalyst stream has a temperature of 170° C. in the decanter with high water content available.

A technique that is often used in the art to regenerate the catalyst is combustion of the oligomers stuck to the catalyst surface (coked catalyst), where the accumulated oligomer is burned from the catalyst surface.

However this technique requires extra energy for the combustion and puts and shortens the catalyst lifespan.

The invention claimed is:

1. A process for synthesizing lactide, comprising the steps of:
adding thermal energy to at least one aromatic solvent;
adding the at least one aromatic solvent to at least one reactor;
providing one or more components comprising lactic acid and the at least one aromatic solvent;
converting at least part of the lactic acid into lactide and water; and
recovering at least part of the lactide;
wherein the at least one aromatic solvent is provided in the at least one reactor independently from the lactic acid by a separate entry into the at least one reactor;
wherein the step of converting at least part of the lactic acid into lactide and water is performed in one step; and
wherein prior to the step of adding the at least one aromatic solvent to the at least one reactor, the aromatic solvent has a temperature of at least 5° C. and at most 100° C. greater than the temperature of the lactic acid.

2. The process according to claim 1, wherein the process is an industrial process for synthesizing lactide.

3. The process according to claim 1, wherein the one or more components are provided to at least two reactors.

4. The process according to claim 3, comprising the step of recovering at least part of the water, wherein the at least part of the water is recovered between the at least two reactors.

5. The process according to claim 4, wherein at least 50% of the water is recovered between the at least two reactors, based on the total amount of water exiting the first reactor of the at least two reactors.

6. The process according to claim 3, wherein the at least one aromatic solvent is divided into at least two solvent fractions, and wherein each solvent fraction is separately provided to each reactor of the at least two reactors.

7. The process according to claim 6, wherein the at least two solvent fractions comprise a first solvent fraction and a second solvent fraction, and wherein at least part of the thermal energy is added to the first solvent fraction.

8. The process according to claim 7, wherein the at least two solvent fractions comprise a first solvent fraction and a second solvent fraction, and wherein at least part of the thermal energy is added to the second solvent fraction.

9. The process according to claim 7, comprising the steps of;
providing a first solvent fraction comprising at least 50% and at most 100% of the at least one aromatic solvent to the first reactor of the at least two reactors; and
providing a second solvent fraction comprising at least 0% and at most 50% of the at least one aromatic solvent to the second reactor of the at least two reactors with % based on the total sum weight of the first solvent fraction and the second solvent fraction.

10. The process according to claim 1, wherein the thermal energy added to the at least one aromatic solvent is at least partly recovered thermal energy.

11. The process according to claim 1, comprising the steps of:
providing one or more components to at least one reactor, the one or more components comprising lactic acid;
converting at least part of the lactic acid into lactide and water and into lactic acid oligomers;
recovering at least part of the lactide;
recovering at least part of the water and at least part of the lactic acid oligomers;
adding a feed, optionally comprising lactic acid oligomers, and optionally comprising water, to the recovered water and the recovered lactic acid oligomers, and mixing the feed with the recovered water and the recovered lactic acid oligomers to form a mixture;
converting at least part of the lactic acid oligomers in the mixture into lactic acid and into lactic acid dimer; and
removing at least part of the water from the mixture;
whereby at least part of the remainder of the mixture is provided as one of the one or more components that are provided to the at least one reactor.

12. The process according to claim 1, comprising the steps of:
adding thermal energy to at least one of one or more components;

providing the one or more components to at least one reactor, the one or more components comprising lactic acid;

converting at least part of the lactic acid into lactide and water;

recovering at least part of the lactide;

recovering at least part of the thermal energy; and adding the recovered thermal energy to at least one of the one or more components.

13. The process according to claim 1, comprising the steps of:

providing one or more components to at least one reactor, the one or more components comprising lactic acid;

converting at least part of the lactic acid into lactide and water;

recovering at least part of the lactide; and recovering at least part of the water;

wherein the step of recovering at least part of the water comprises a decantation step, with the proviso that the step of recovering at least part of the water does not comprise an azeotropic distillation step.

\* \* \* \* \*